(12) United States Patent
Branch et al.

(10) Patent No.: US 11,666,501 B2
(45) Date of Patent: *Jun. 6, 2023

(54) DEVICES AND METHODS FOR ASSISTING PRONATION AND/OR SUPINATION

(71) Applicant: ERMI, Inc., Atlanta, GA (US)

(72) Inventors: Thomas P. Branch, Atlanta, GA (US); Shaun Kevin Stinton, Chamblee, GA (US); Edward Dittmar, Marietta, GA (US); Nathaniel Kinsey DeJarnette, Atlanta, GA (US)

(73) Assignee: Ermi LLC, Atlanta, GA (US)

( * ) Notice: Subject to any disclaimer, the term of this patent is extended or adjusted under 35 U.S.C. 154(b) by 833 days.

This patent is subject to a terminal disclaimer.

(21) Appl. No.: 16/358,151

(22) Filed: Mar. 19, 2019

(65) Prior Publication Data
US 2019/0274910 A1 Sep. 12, 2019

Related U.S. Application Data

(63) Continuation of application No. 14/569,627, filed on Dec. 13, 2014, now Pat. No. 10,278,881.

(60) Provisional application No. 61/915,264, filed on Dec. 12, 2013.

(51) Int. Cl.
A61H 1/02 (2006.01)

(52) U.S. Cl.
CPC ......... *A61H 1/0274* (2013.01); *A61H 1/0277* (2013.01); *A61H 2001/0203* (2013.01); *A61H 2001/0207* (2013.01); *A61H 2201/1676* (2013.01)

(58) Field of Classification Search
CPC ........ A61H 1/0285; A61H 2001/02023; A61H 2001/0207
See application file for complete search history.

(56) References Cited

U.S. PATENT DOCUMENTS

| 4,772,012 A | 9/1988 | Chesher |
| 4,809,688 A | 3/1989 | Aymerica del Valle et al. |
| 5,103,811 A | 4/1992 | Crupi, Jr. |

(Continued)

FOREIGN PATENT DOCUMENTS

| WO | 9504507 A1 | 2/1995 |
| WO | 9945864 A1 | 9/1999 |

(Continued)

*Primary Examiner* — LaToya M Louis
(74) *Attorney, Agent, or Firm* — Shumaker, Loop & Kendrick, LLP; Patrick B. Horne

(57) ABSTRACT

Devices manipulate a hand of a user to provide pronation or supination assistance. Embodiments include an anchor; a hand engagement member operatively attached to the anchor and configured to receive and engage the hand of the user; a force applicator having a member portion and an anchor portion opposite the member portion, the force applicator attached to the hand engagement member proximate its member portion and attached to the anchor proximate its anchor portion; and a force application mechanism attached to the anchor and configured to cause a force to be applied to the force applicator causing the hand engagement member to manipulate the hand of the user to provide pronation or supination assistance. In some embodiments, the force application mechanism includes a non-incremental rotary mechanism. In some embodiments, a flexible tethering member attaches the anchor to the hand engagement member.

20 Claims, 34 Drawing Sheets

(56) References Cited

U.S. PATENT DOCUMENTS

| | | |
|---|---|---|
| 5,328,448 A | 7/1994 | Gray, Sr. |
| 5,364,323 A | 11/1994 | Liu |
| 5,476,439 A | 12/1995 | Robinson |
| 5,658,241 A | 8/1997 | Deharde et al. |
| 5,662,594 A | 9/1997 | Rosenblatt |
| 5,681,269 A | 10/1997 | Basaj et al. |
| 5,697,892 A | 12/1997 | Torgerson |
| 5,738,636 A | 4/1998 | Saringer et al. |
| 5,817,040 A | 10/1998 | Hess et al. |
| 5,820,577 A | 10/1998 | Taylor |
| 5,823,886 A | 10/1998 | Murray |
| 5,848,979 A | 12/1998 | Bonutti et al. |
| 5,891,061 A | 4/1999 | Kaiser |
| 5,891,079 A | 4/1999 | Barnes |
| 5,899,870 A | 5/1999 | Deirmendjian et al. |
| 5,951,499 A | 9/1999 | Saringer et al. |
| 5,957,813 A | 9/1999 | Macdonald |
| 5,976,058 A | 11/1999 | Gustafson |
| 6,001,075 A | 12/1999 | Clemens et al. |
| 6,063,087 A | 5/2000 | Agee et al. |
| 6,080,122 A | 6/2000 | Gulledge |
| 6,117,097 A | 9/2000 | Ruiz |
| 6,142,964 A | 11/2000 | Gilmour |
| 6,179,799 B1 | 1/2001 | Doran |
| 6,196,985 B1 | 3/2001 | Slautterback |
| 6,293,918 B1 | 9/2001 | Wang |
| 6,506,172 B1 | 1/2003 | Hepburn et al. |
| 6,537,237 B1 | 3/2003 | Hopkins et al. |
| 6,565,563 B1 | 5/2003 | Agee et al. |
| 6,689,080 B2 | 2/2004 | Castillo |
| 6,740,051 B2 | 5/2004 | Hepburn et al. |
| 6,793,641 B2 | 9/2004 | Freeman et al. |
| 6,921,377 B2 | 7/2005 | Bonutti |
| 6,969,365 B2 | 11/2005 | Scorvo |
| 7,001,352 B2 | 2/2006 | Farrell et al. |
| 7,083,583 B2 | 8/2006 | Opahle et al. |
| 7,090,650 B2 | 8/2006 | Ou et al. |
| 7,101,347 B2 | 9/2006 | Culhane et al. |
| 7,112,179 B2 | 9/2006 | Bonutti et al. |
| 7,156,818 B2 | 1/2007 | Salmon et al. |
| 7,156,819 B2 | 1/2007 | Sieller et al. |
| 7,404,804 B2 | 7/2008 | Bonutti |
| 7,404,805 B2 | 7/2008 | Weiss |
| 7,452,342 B2 | 11/2008 | Bonutti et al. |
| 7,491,186 B2 | 2/2009 | Zeide et al. |
| 7,517,329 B2 | 4/2009 | Salmon et al. |
| 7,534,219 B2 | 5/2009 | Stearns |
| 7,537,547 B1 | 5/2009 | Hosick et al. |
| 7,537,577 B2 | 5/2009 | Phelan et al. |
| 7,601,130 B2 | 10/2009 | Farrell et al. |
| 7,621,883 B2 | 11/2009 | Duren et al. |
| 7,699,797 B2 | 4/2010 | Nordt, III et al. |
| 7,704,219 B2 | 4/2010 | Nordt, III et al. |
| 7,833,183 B2 | 11/2010 | Padova |
| 7,878,998 B2 | 2/2011 | Nordt, III et al. |
| 7,892,194 B2 | 2/2011 | Farrell et al. |
| 7,914,475 B2 | 3/2011 | Wyatt et al. |
| 7,922,680 B2 | 4/2011 | Nordt, III et al. |
| 7,955,286 B2 | 6/2011 | Bonutti et al. |
| 7,967,765 B2 | 6/2011 | Nathanson |
| 7,981,067 B2 | 7/2011 | Bonutti et al. |
| 7,993,294 B2 | 8/2011 | Hassler et al. |
| 8,012,108 B2 | 9/2011 | Bonutti et al. |
| 8,016,781 B2 | 9/2011 | Ingimundarson et al. |
| 8,038,637 B2 | 10/2011 | Bonutti |
| 8,070,702 B2 | 12/2011 | Farrell et al. |
| 8,147,438 B2 | 4/2012 | Livolsi et al. |
| 8,172,781 B2 | 5/2012 | Oddou et al. |
| 8,206,329 B2 | 6/2012 | Bonutti et al. |
| 8,216,168 B2 | 6/2012 | Farrell et al. |
| 8,231,560 B2 | 7/2012 | Ingimundarson et al. |
| 8,235,928 B2 | 8/2012 | Padova |
| 8,246,559 B2 | 8/2012 | Hoffman et al. |
| 8,246,560 B2 | 8/2012 | Gaylord et al. |
| 8,257,283 B2 | 9/2012 | Kaiser |
| 8,273,043 B2 | 9/2012 | Bonutti et al. |
| 8,328,743 B2 | 12/2012 | Farrell et al. |
| 8,328,744 B2 | 12/2012 | Farrell et al. |
| 8,348,810 B2 | 1/2013 | Land et al. |
| 8,419,670 B2 | 4/2013 | Downing |
| 8,425,440 B2 | 4/2013 | DeToro et al. |
| 8,460,222 B2 | 6/2013 | Garrec |
| 8,517,965 B2 | 8/2013 | Doty et al. |
| 8,574,137 B2 | 11/2013 | Chen et al. |
| 8,591,443 B2 | 11/2013 | Bonutti et al. |
| 8,622,939 B2 | 1/2014 | Nguyen |
| 8,622,945 B2 | 1/2014 | Meals |
| 8,652,076 B2 | 2/2014 | Land et al. |
| 8,678,980 B2 | 3/2014 | Land et al. |
| 8,679,043 B2 | 3/2014 | Bonutti |
| 8,679,045 B2 | 3/2014 | Dao |
| 8,702,634 B2 | 4/2014 | Crompton |
| 8,708,939 B2 | 4/2014 | Bonutti et al. |
| 8,740,829 B2 | 6/2014 | Lee et al. |
| 8,753,301 B2 | 6/2014 | Tran |
| 8,771,212 B1 | 7/2014 | Garris et al. |
| 8,784,343 B2 | 7/2014 | Bonutti et al. |
| 8,784,348 B2 | 7/2014 | Farrell et al. |
| 8,814,816 B2 | 8/2014 | Bonutti et al. |
| 8,821,420 B1 | 9/2014 | Callahan |
| 8,827,873 B2 | 9/2014 | Arnstein |
| 8,864,692 B2 | 10/2014 | Ingimundarson et al. |
| 8,864,695 B2 | 10/2014 | Thornton |
| 8,882,688 B1 | 11/2014 | Ancinec |
| 2002/0151832 A1 | 10/2002 | Wedge, Jr. |
| 2006/0264792 A1 | 11/2006 | Bonn |
| 2009/0054820 A1 | 2/2009 | Weltner et al. |
| 2011/0152736 A1 | 6/2011 | Ng |
| 2012/0059298 A1 | 3/2012 | Hoffman et al. |
| 2012/0215145 A1 | 8/2012 | Ingimundarson et al. |
| 2012/0323148 A1 | 12/2012 | Kaiser |
| 2013/0072829 A1 | 3/2013 | Fausti et al. |
| 2013/0110020 A1 | 5/2013 | Ingimundarson et al. |
| 2013/0144195 A1 | 6/2013 | Cehic |
| 2013/0317395 A1 | 11/2013 | Laflin |
| 2013/0338547 A1 | 12/2013 | Shimizuhira et al. |
| 2013/0338548 A1 | 12/2013 | Nakamura |
| 2014/0194799 A1 | 7/2014 | Bonutti et al. |
| 2014/0303527 A1 | 10/2014 | Bonutti et al. |

FOREIGN PATENT DOCUMENTS

| | | |
|---|---|---|
| WO | 2004041485 A1 | 5/2004 |
| WO | 2006058442 A8 | 8/2006 |
| WO | 2006138142 A2 | 12/2006 |
| WO | 2006138142 A3 | 12/2006 |
| WO | 2009015364 A1 | 1/2009 |
| WO | 2011156773 A1 | 12/2011 |
| WO | 2013163733 A1 | 11/2013 |
| WO | 2014033613 A3 | 3/2014 |
| WO | 2014146766 A1 | 9/2014 |

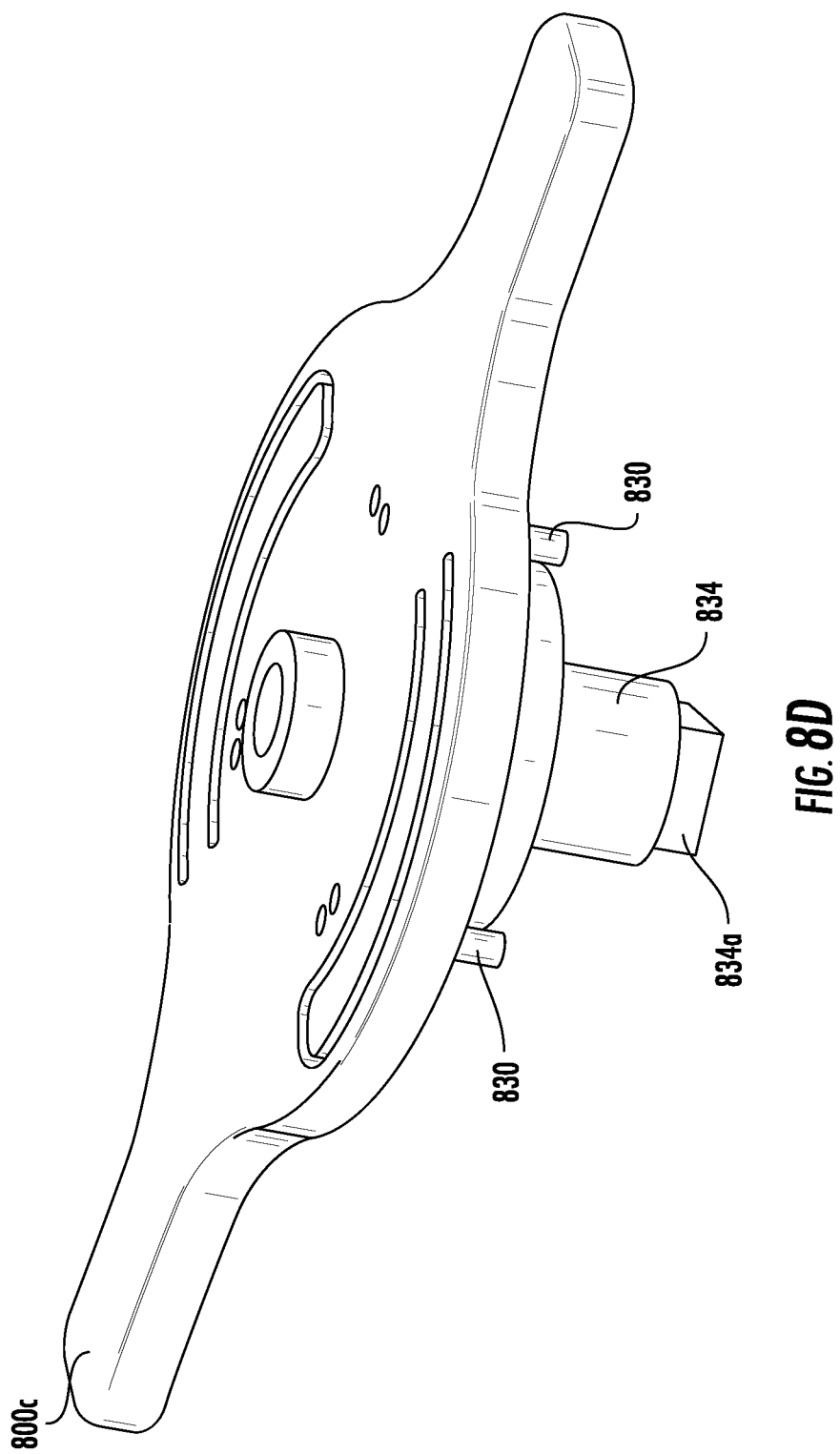

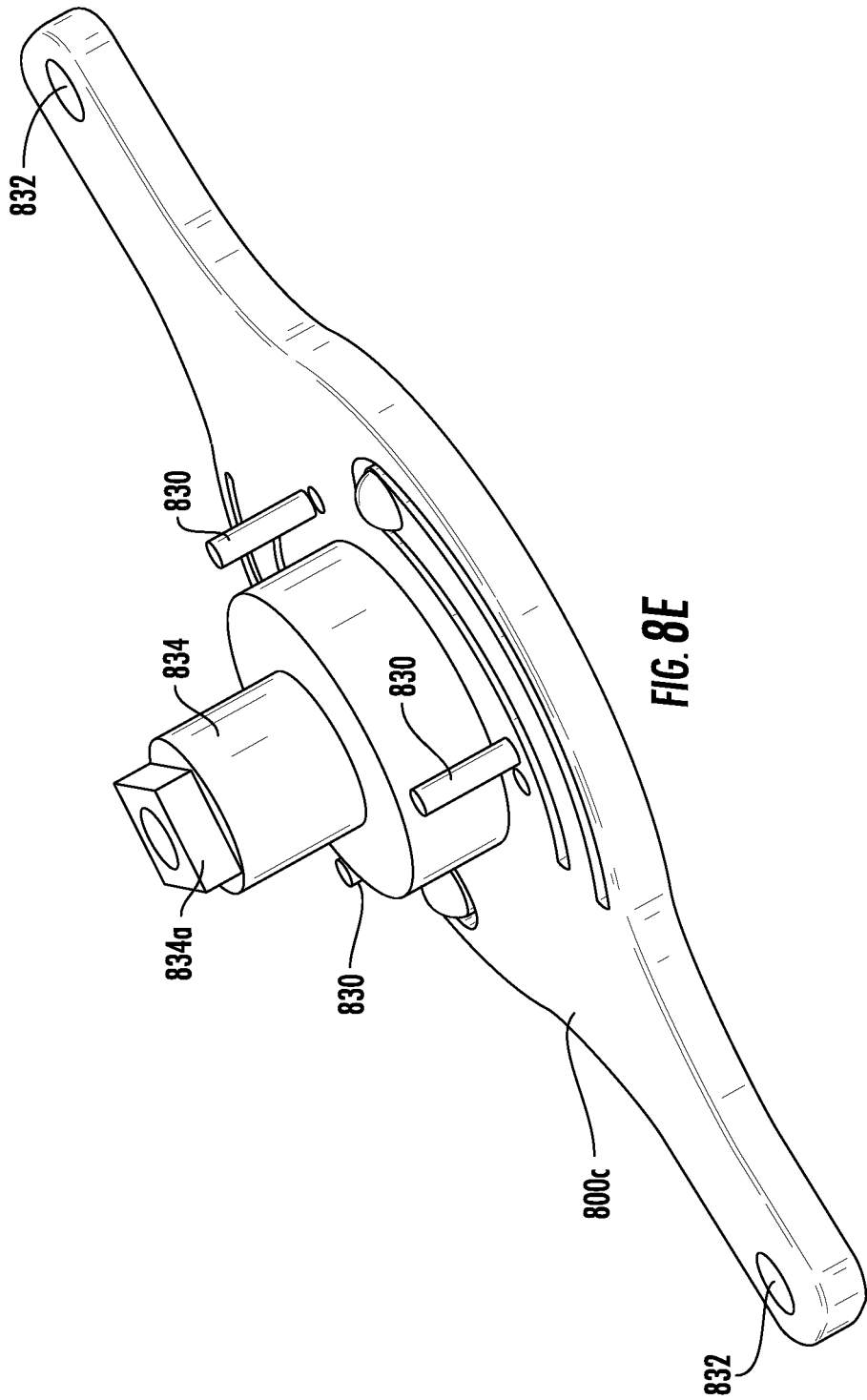

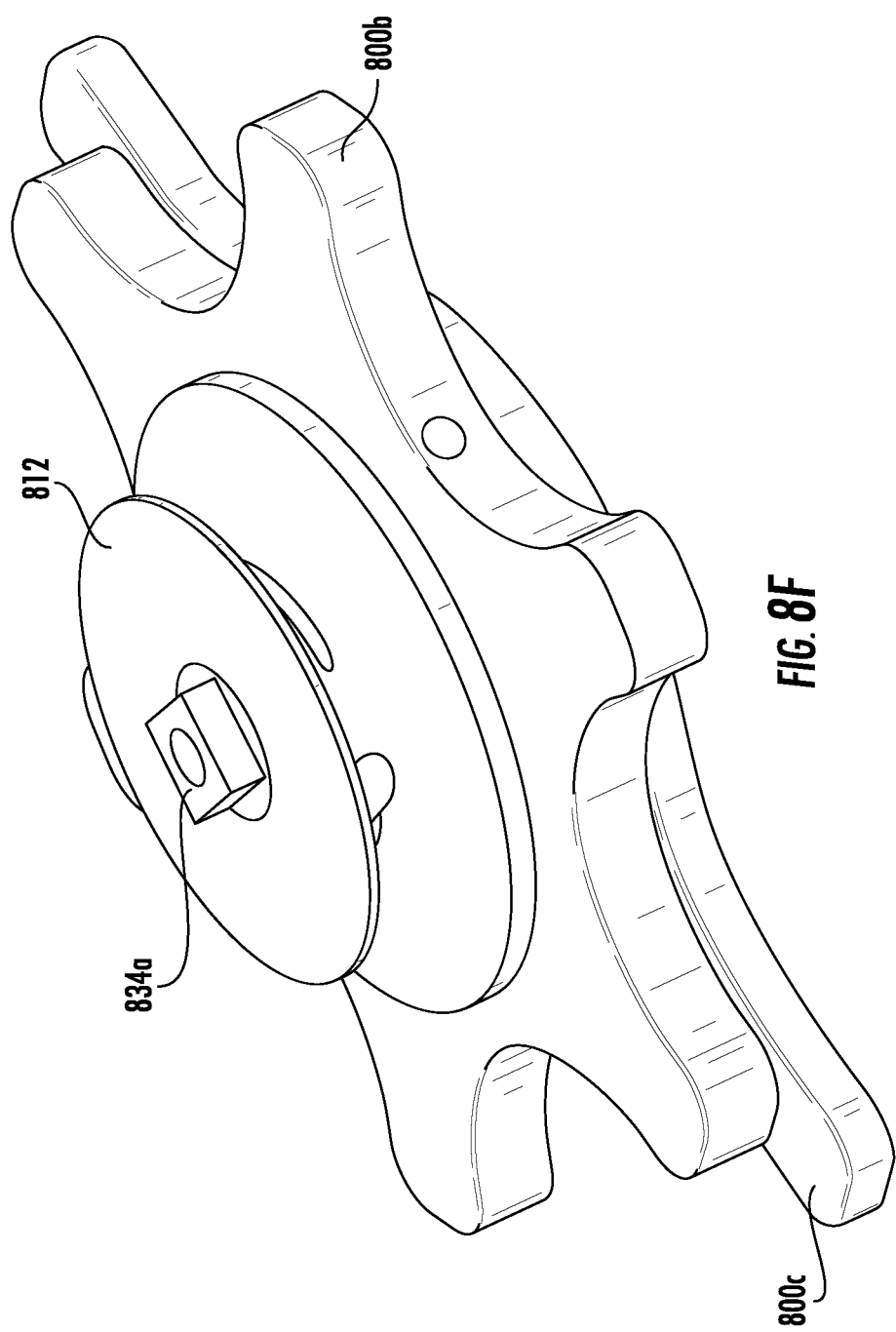

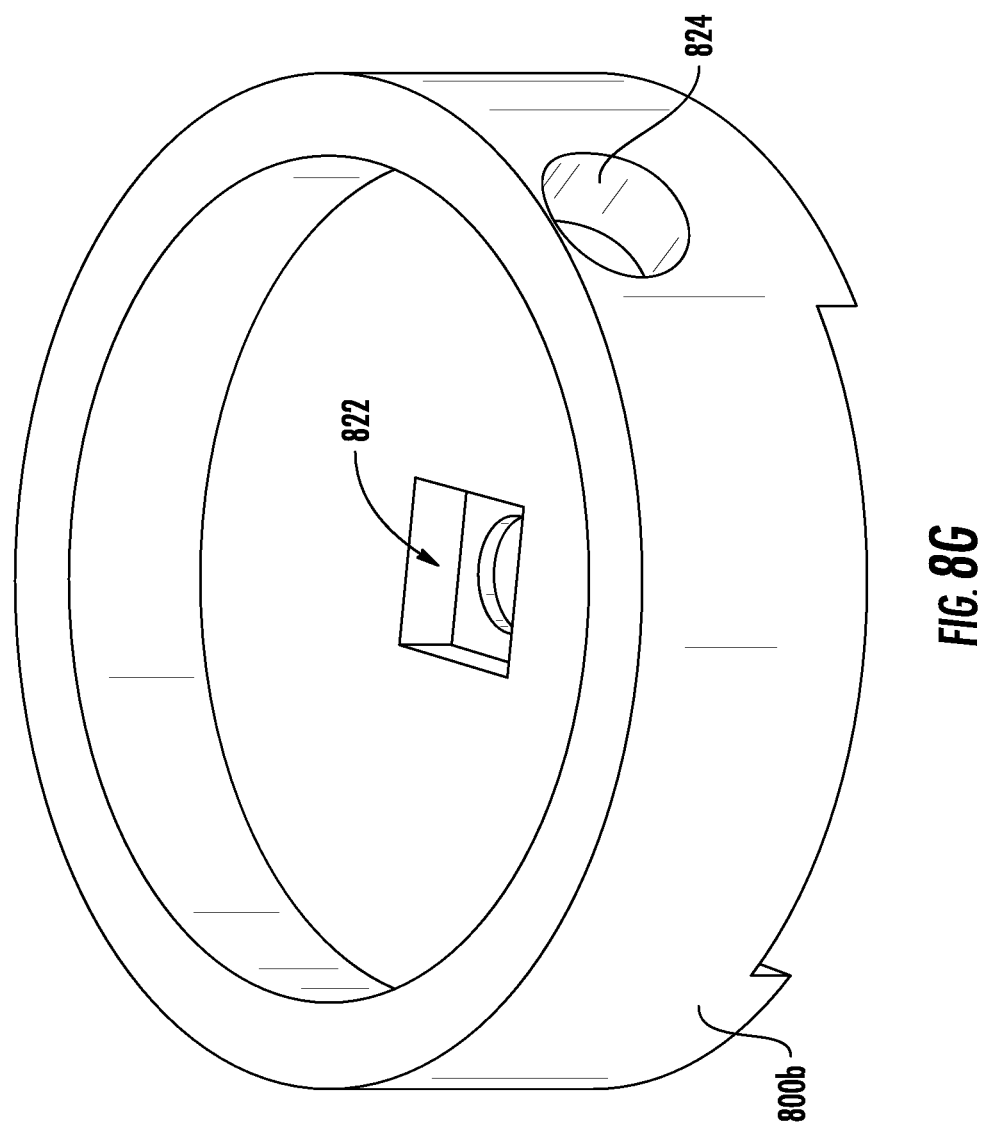

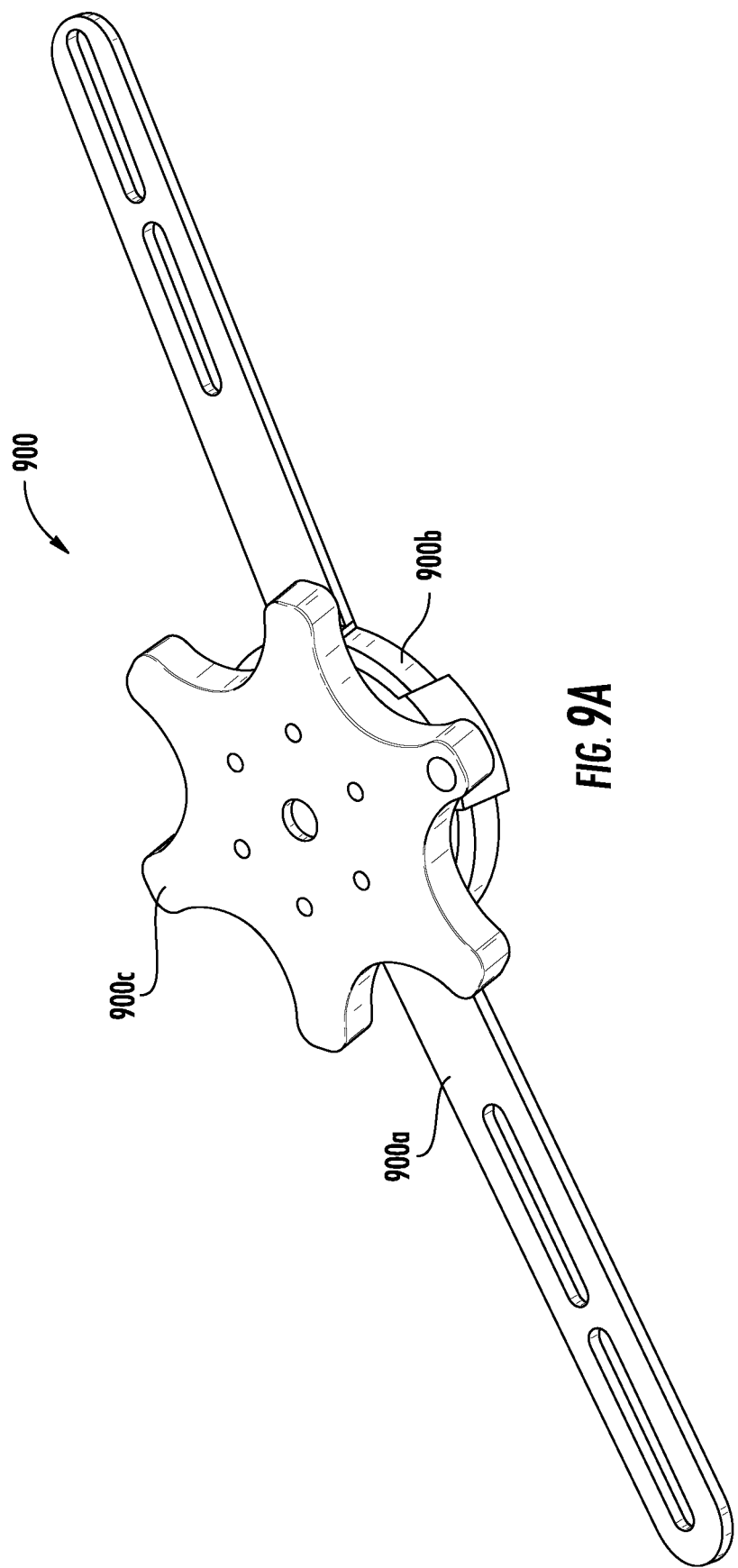

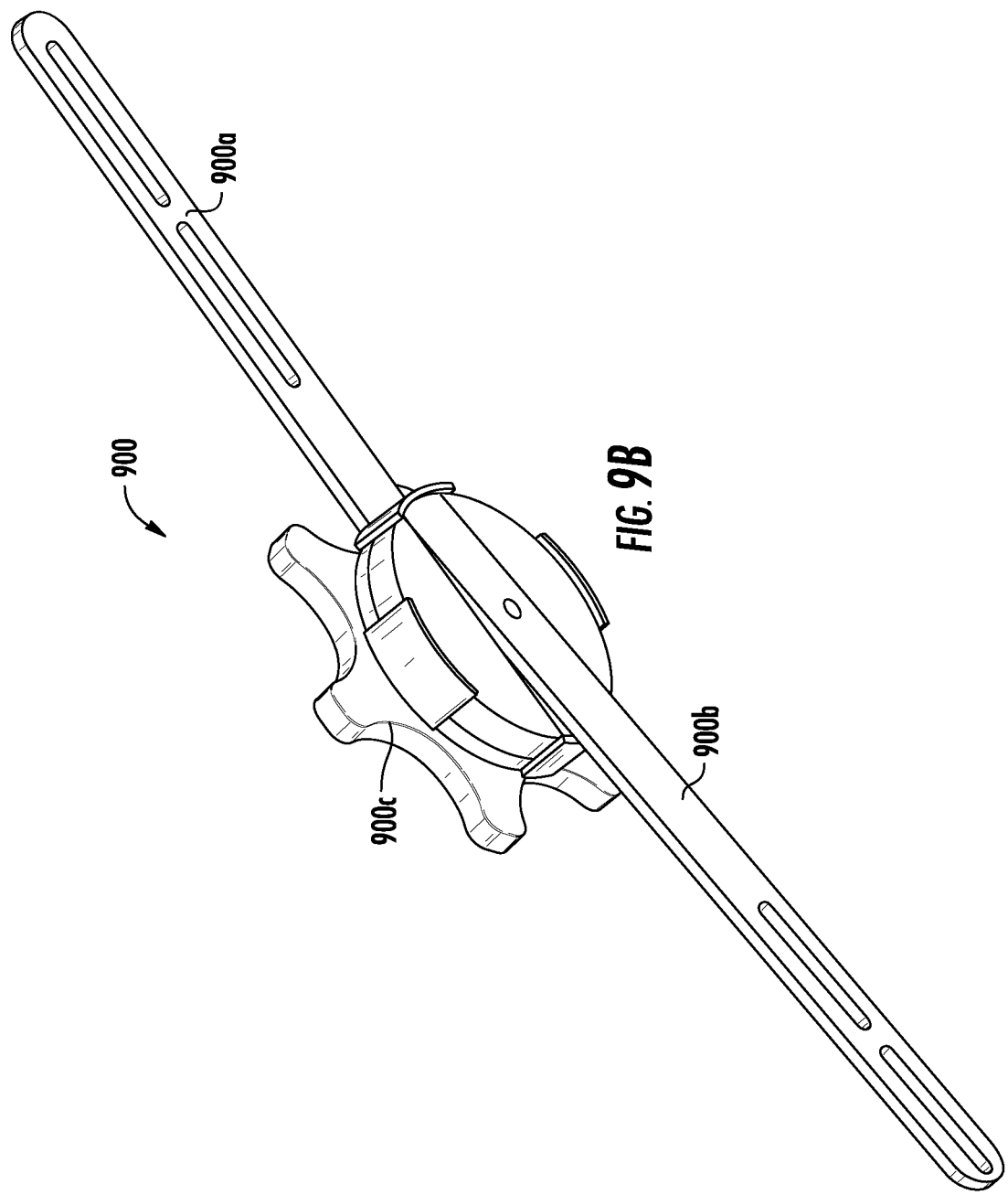

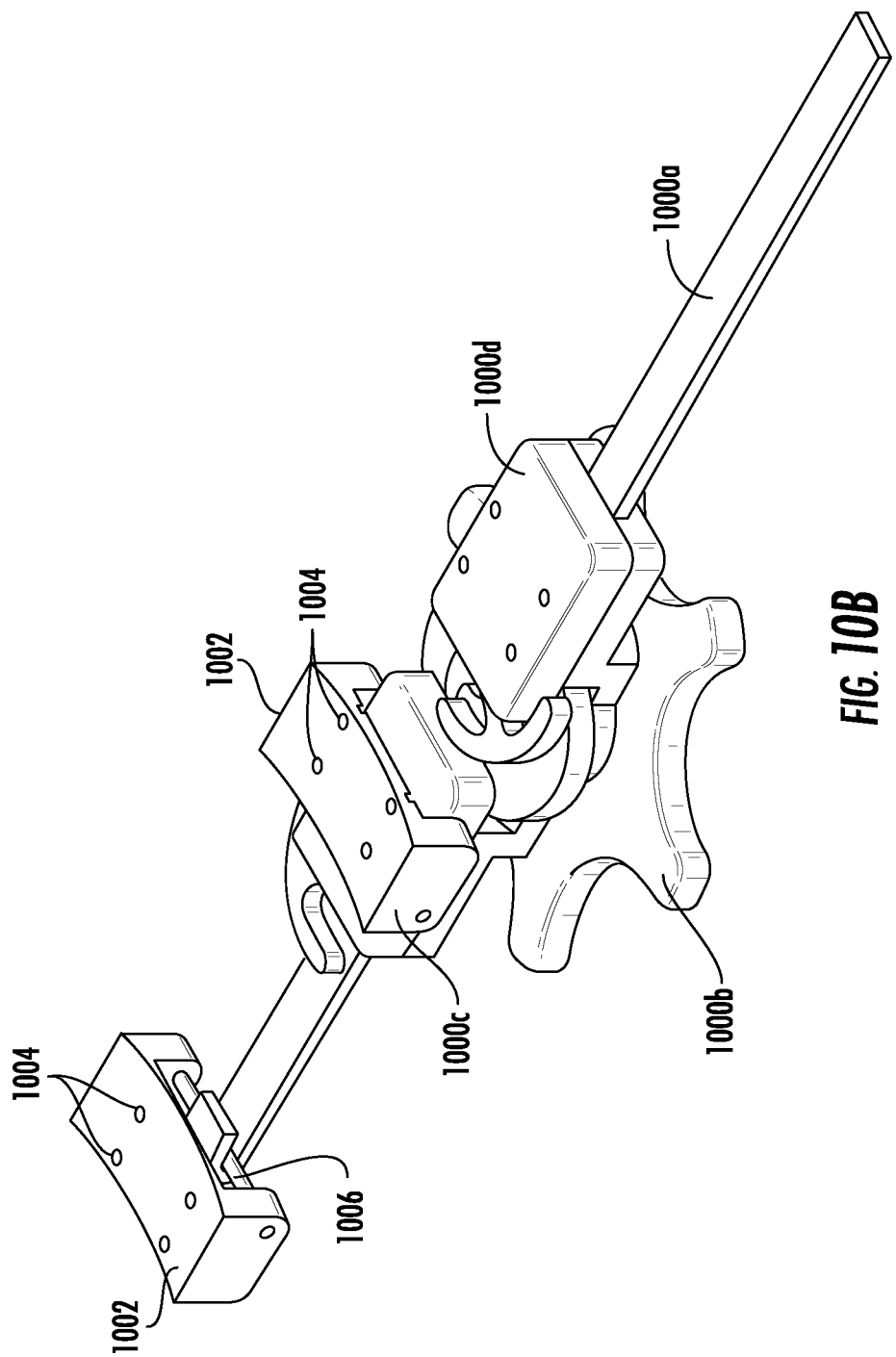

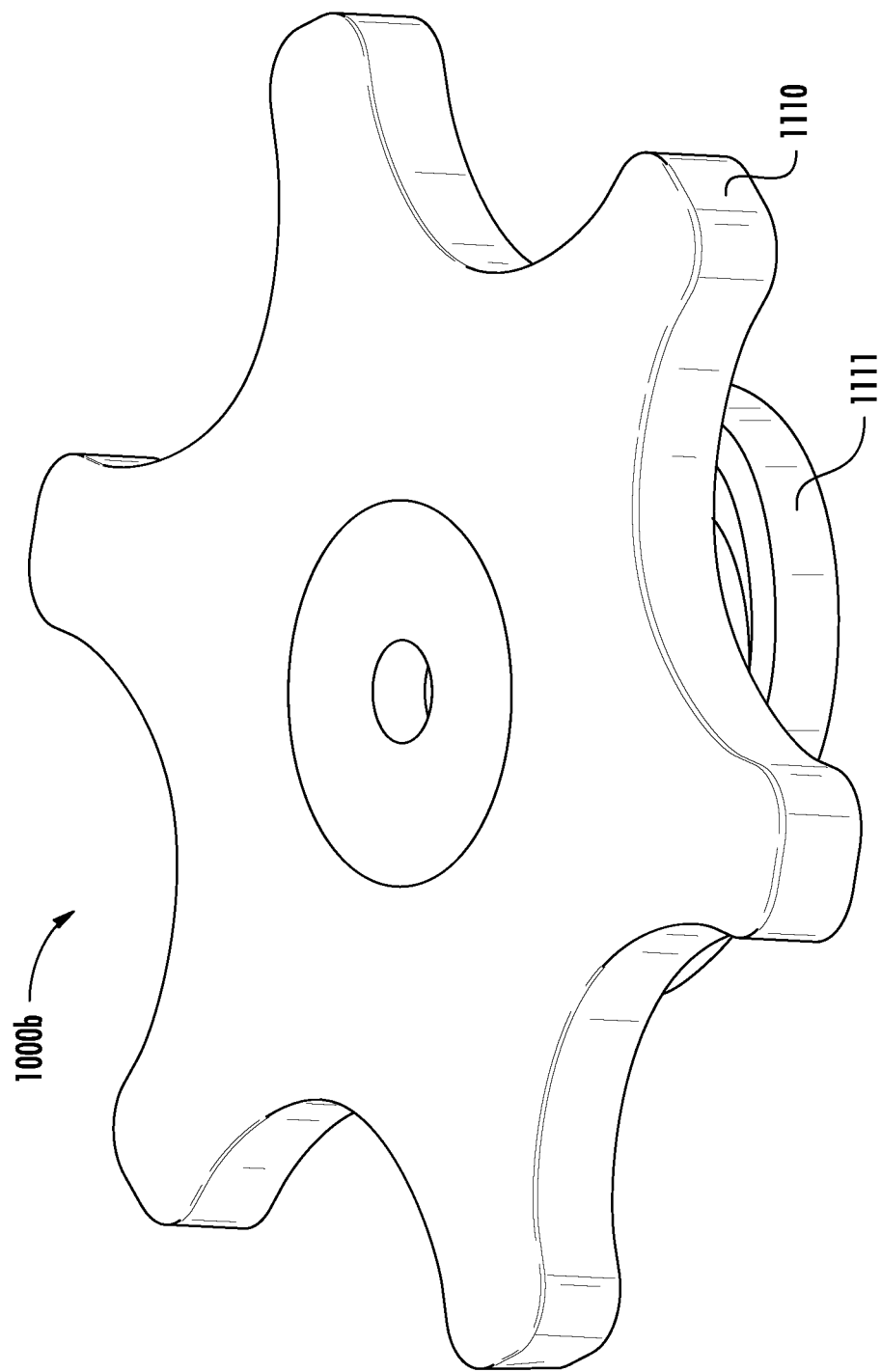

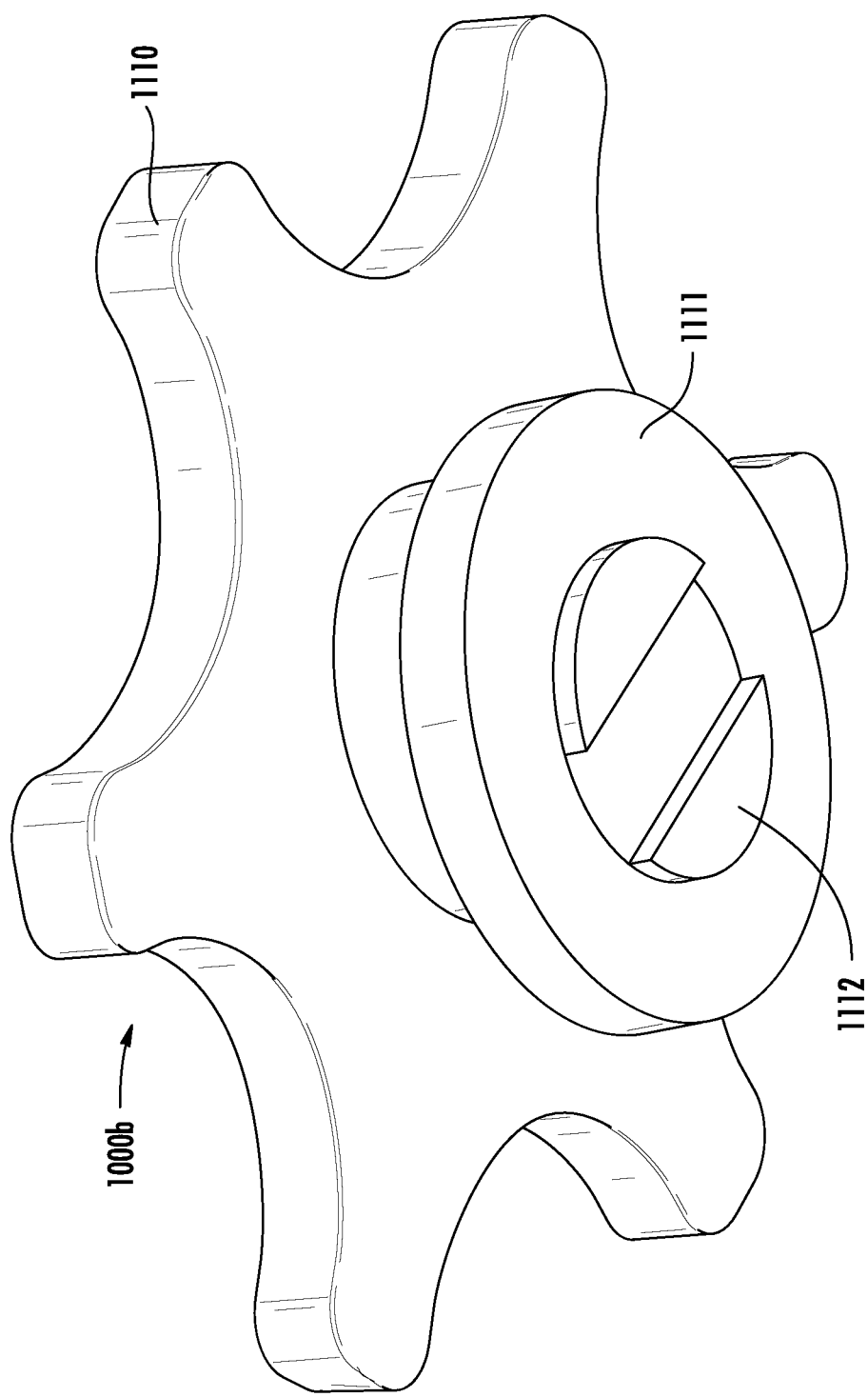

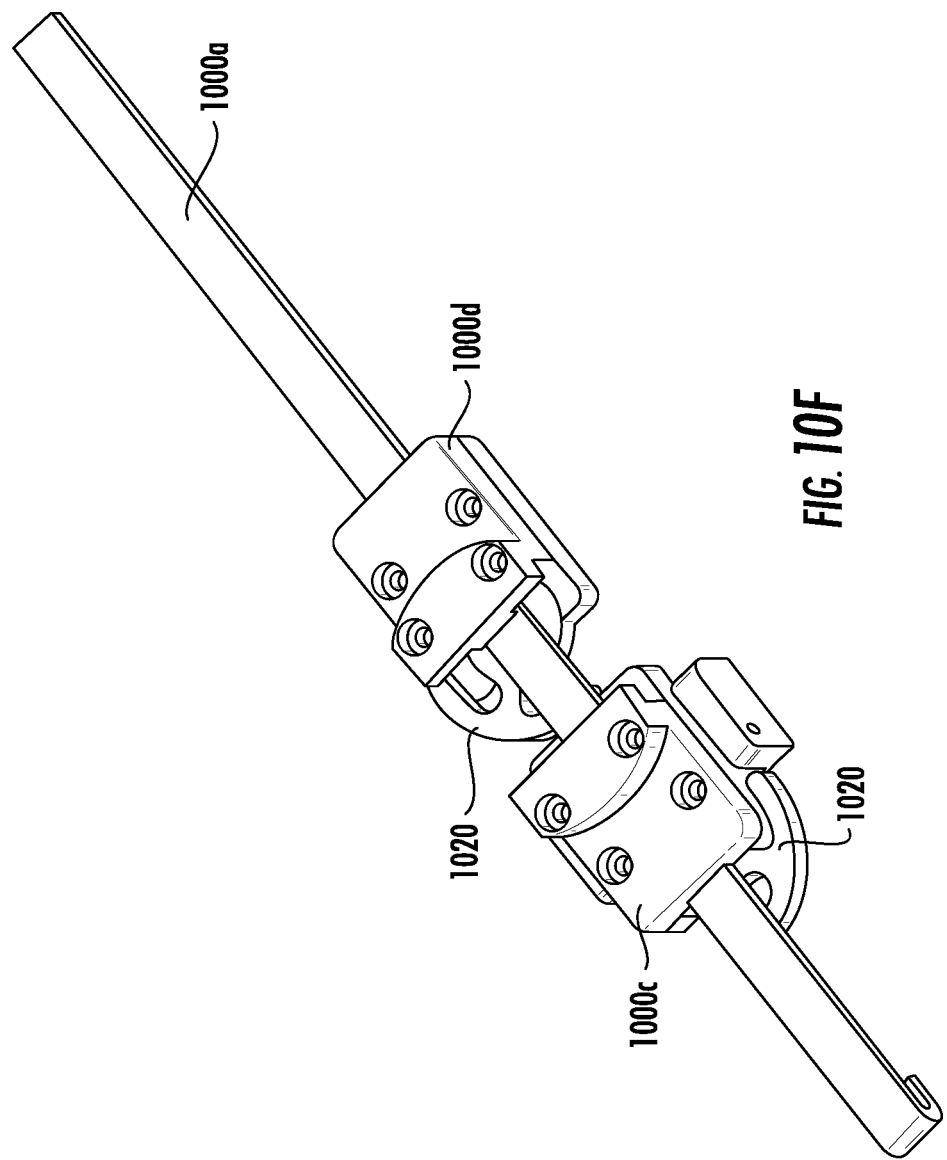

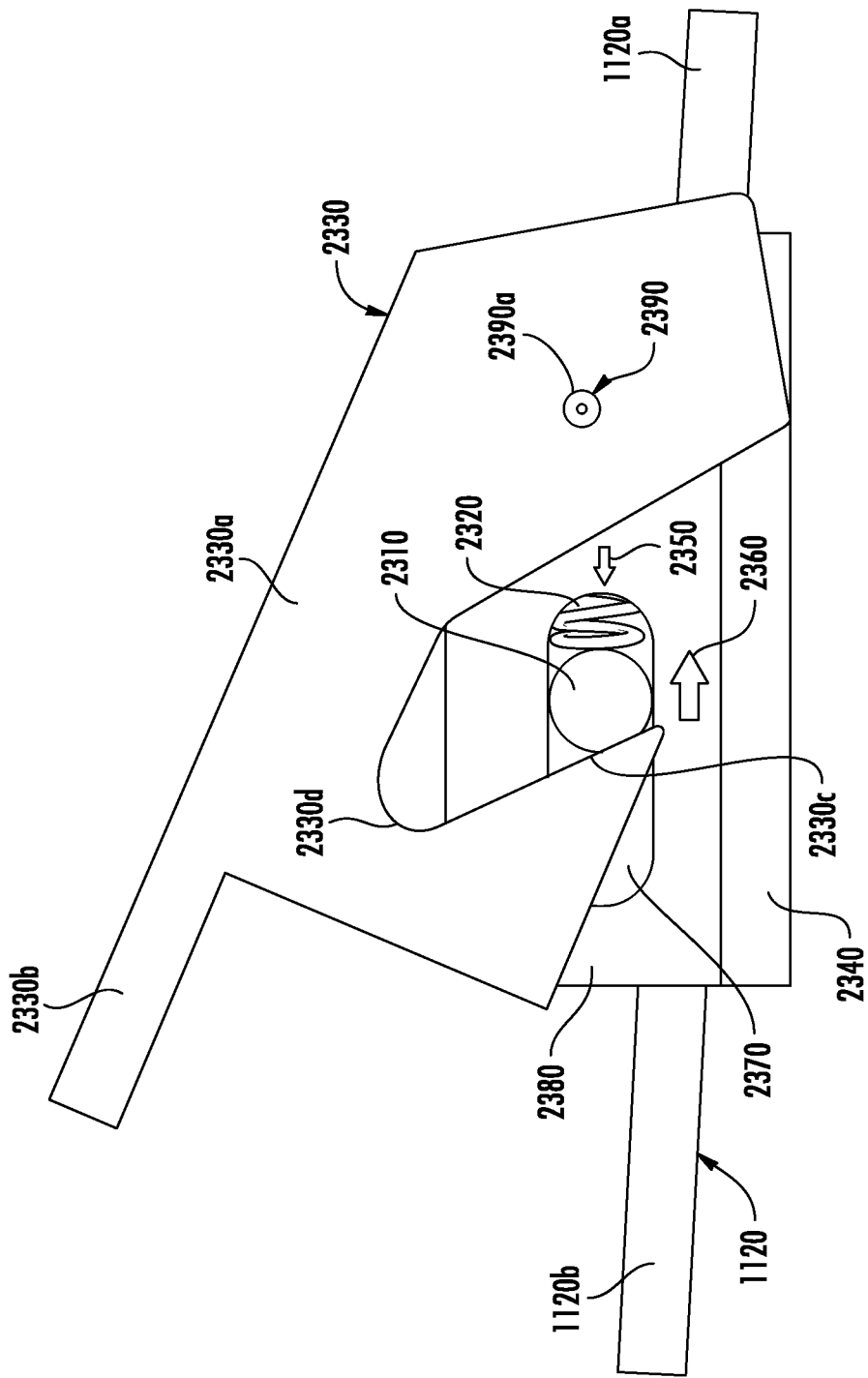

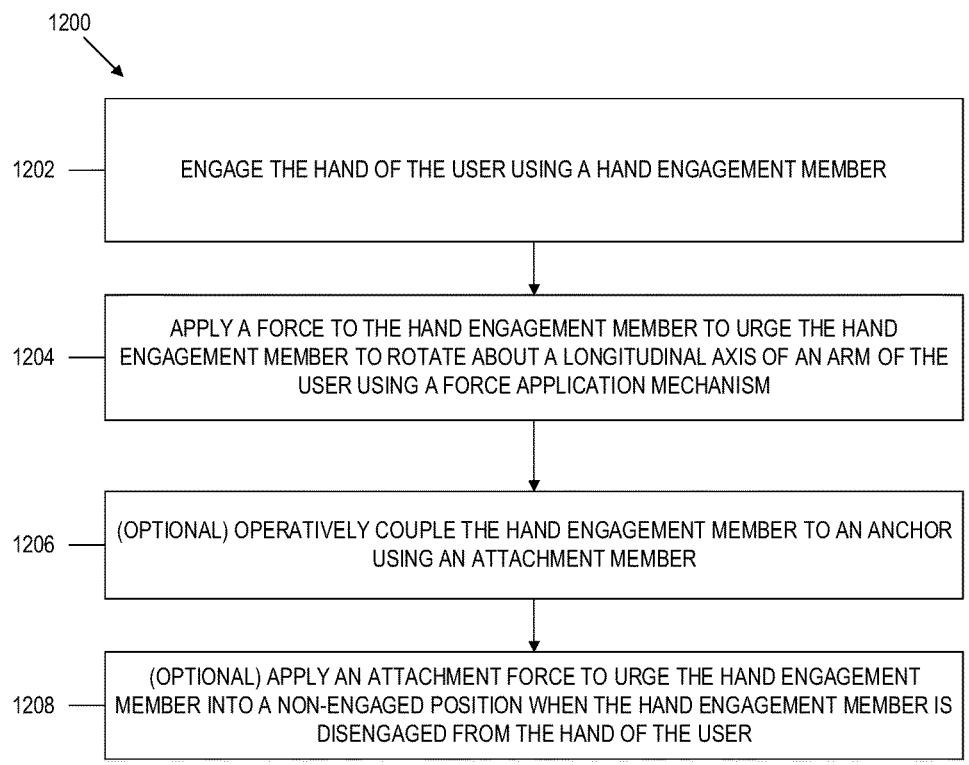

DEVICES AND METHODS FOR ASSISTING PRONATION AND/OR SUPINATION

CLAIM OF PRIORITY UNDER 35 U.S.C. § 119

The present application for patent claims priority to Provisional Application No. 61/915,264, entitled "Upper Extremity Support and Range of Motion Device and Methods for Using Same," filed Dec. 12, 2013, and U.S. patent application Ser. No. 14/569,627, entitled "Devices and Methods for Assisting Pronation and/or Supination" filed Dec. 13, 2014, both of which are assigned to the assignee hereof and hereby expressly incorporated by reference in their entirety.

TECHNICAL FIELD

This invention relates generally to orthotic devices and more particularly to orthotic devices designed to improve and promote gains in range of motion in a joint by use of mechanical lever systems and/or pneumatic systems.

BACKGROUND

When a joint is damaged either from an injury event or through surgical intervention, scar tissue may form and limit the motion of the joint. This loss of motion can greatly affect a person's quality of life by limiting their ability to accomplish their normal activities of daily living. Traditionally, orthotics are separated into two categories: those that support and protect limbs and those that attempt to return range of motion to the joint by application of force.

Different joints are capable of moving in different directions, and the full range of motion of a joint depends upon the anatomy of that joint and on the particular genetics of each individual. Joint motion can generally be classified as linear or rotational. For example, linear joint motions include flexion and extension where flexion is defined as a bending of the joint and extension is often defined as a straightening of the joint. Rotational motions include pronation and supination, which is where the hand rotates around the longitudinal axis of the forearm placing the palm up or the palm down.

Conventional orthotic devices have attempted to provide support across a joint, traditionally utilizing a rigid member or hinged joint. Orthotics aim to protect the joint by supporting the joint.

Some devices use a hinge system to apply a low load force on the joint by tightening a spring and thus stretching accumulated scar tissue over a long period of time. Some use a cuff for each limb segment and are uncomfortable and must be worn for hours at a time to be effective.

BRIEF SUMMARY

Embodiments of the invention are directed to a device for manipulating a hand of a user to provide pronation or supination assistance, the device comprising an anchor; a hand engagement member operatively coupled to the anchor and configured to receive and engage the hand of the user; a force applicator comprising a member portion and an anchor portion opposite the member portion, the force applicator operatively coupled to the hand engagement member proximate its member portion and operatively coupled to the anchor proximate its anchor portion; and a force application mechanism operatively coupled to the anchor and configured to apply a force to the force applicator causing the hand engagement member to manipulate the hand of the user to provide the pronation or supination assistance.

In some embodiments, the hand engagement member is configured to receive and engage only the hand of the user without engaging a wrist or a forearm of the user.

In some embodiments, the hand engagement member is configured to receive and engage the hand of the user and remain engaged with the hand of the user as the force is applied by the force applicator and the force application mechanism.

In some embodiments, the device includes an attachment member that operatively couples the hand engagement member to the anchor. In some such embodiments, the attachment member comprises a tethering member that tethers the hand engagement member to the anchor. In other embodiments, the attachment member is configured to apply a force to the hand engagement member to urge the hand engagement member into a non-engaged position when the hand engagement member is disengaged with the hand of the user. In yet other embodiments, the hand engagement member is configured to move from a disengaged position to a first engaged position when it receives the hand of the user.

In some embodiments, the hand engagement member is configured to move from a first engaged position to a second engaged position when the force is applied by the force application mechanism. In some embodiments, the first engaged position provides a lower degree of pronation or supination to the wrist of the user than the second engaged position.

In other embodiments, the anchor comprises an anchor hand-facing surface; the hand engagement member, when engaging the hand of the user, engages at least a portion of a palm side or at least a portion of a dorsal side of the hand of the user, and defines an engagement plane substantially parallel with a frontal plane of the hand of the user; and the anchor hand-facing surface and the engagement plane define an engagement angle. In some such embodiments, the engagement angle is a first value when the hand engagement member is in the first engaged position; the engagement angle is a second value when the hand engagement member is in the second engaged position; and the first value is greater than the second value, thereby providing pronation or supination assistance to the wrist of the user when the hand engagement member is moved from the first engaged position to the second engaged position.

In other such embodiments, the hand engagement member, when engaging the hand of the user, engages at least a portion of the palm side, at least a portion of the ulnar side and at least a portion of the dorsal side of the hand of the user, thereby forming a hand receptacle. In some such embodiments, the hand receptacle comprises a substantially planar palm portion configured to engage at least a portion of the palm side of the hand of the user; a U-shaped ulnar portion connected to the palm portion, the ulnar portion configured to engage at least a portion of the ulnar side of the hand of the user; and a substantially planar dorsal portion connected to the ulnar portion, the dorsal portion configured to engage at least a portion of the dorsal side of the hand of the user.

In some embodiments, the hand receptacle is substantially taco-shell-shaped.

In some embodiment, when the hand engagement member is moved from the first engaged position to the second engaged position, the hand engagement member causes the hand to rotate or move in an arcuate or substantially arcuate range of motion substantially about a longitudinal axis of an arm of the user. In some such embodiments, when the hand engagement member is moved from the first engaged position to the second engaged position, the hand engagement member allows the hand to rotate or move in an arcuate or substantially arcuate range of motion about one or more axes other than the longitudinal axis of the arm of the user. In other such embodiments, when the hand engagement member is moved from the first engaged position to the second engaged position, the hand engagement member allows the hand to move in a natural range of motion as the arm is pronated or supinated.

In some embodiments, the movement from the first engaged position to the second engaged position comprises rotational or arcuate movement substantially about the longitudinal axis of the arm of the user or substantially about an axis parallel to the longitudinal axis of the arm of the user.

In some embodiments, the force application mechanism comprises a rotary mechanism. In some such embodiments, the rotary mechanism, when turned, applies the force in a continuous or non-incremental fashion. In some such embodiments, the rotary mechanism, when turned, applies the force in an incremental fashion. In some such embodiments, the rotary mechanism comprises a non-incremental rotary friction lock mechanism. In some embodiments, the rotary mechanism comprises a non-incremental rotary harmonic mechanism.

In some embodiments, the force application mechanism is configured to restrict movement of the hand engagement member from the second engaged position to the first engaged position. In some embodiments, the force application mechanism is configured to restrict, completely, movement of the hand engagement member from the second engaged position to the first engaged position.

In some embodiments, a forearm member operatively coupled to the anchor, the forearm member configured to engage a forearm of the user. In some such embodiments, an upper arm member operatively coupled to the forearm member, the upper arm member configured to engage an upper arm operatively coupled to the forearm of the user by an elbow of the user. In some such embodiments, the forearm member and the upper arm member are operatively coupled relative to one another in a moveable configuration, and when engaged with the user, move relative to one another when the user extends or flexes the elbow. In some such embodiments, the forearm member and the upper arm member are operatively coupled relative to one another in a fixed configuration, thereby substantially preventing flexion or extension of the elbow.

According to embodiments of the invention, an orthotic device for manipulating a hand of a user to provide rotational or arcuate pronation or supination assistance about a longitudinal axis or about an axis parallel to the longitudinal axis of an arm of the user, the orthotic device comprising an anchor; a hand engagement member configured to receive and engage the hand of the user; a flexible tethering member connecting the anchor to the hand engagement member; a force applicator comprising a member portion and an anchor portion opposite the member portion, the force applicator attached to the hand engagement member proximate its member portion and attached to the anchor proximate its anchor portion; and a force application mechanism attached to the anchor and configured to apply a force to the force applicator causing the hand engagement member to manipulate the hand of the user to provide pronation or supination assistance.

According to embodiments of the invention, an orthotic device for manipulating a hand of a user to provide rotational or arcuate pronation or supination assistance about a longitudinal axis or about an axis parallel to the longitudinal axis of an arm of the user, the orthotic device comprising an anchor; a hand engagement member configured to receive and engage the hand of the user; an attachment member connecting the anchor to the hand engagement member; a force applicator comprising a member portion and an anchor portion opposite the member portion, the force applicator attached to the hand engagement member proximate its member portion and attached to the anchor proximate its anchor portion; and a force application mechanism comprising a non-incremental, continuous rotary mechanism attached to the anchor and configured to apply a force to the force applicator causing the hand engagement member to manipulate the hand of the user to provide pronation or supination assistance.

According to embodiments of the invention, a method for manipulating a hand of a user to provide pronation or supination assistance, the method comprising engaging the hand of the user using a hand engagement member; and applying a force to the hand engagement member to urge the hand engagement member to rotate about a longitudinal axis of an arm of the user using a force application mechanism, thereby providing pronation or supination assistance.

In some embodiments, the hand engagement member is operatively coupled to an anchor. In some embodiments, engaging comprises engaging the hand without engaging a wrist or a forearm of the user. In some embodiments, engaging comprises continuously engaging, while the force is applied, the hand of the user.

In some embodiments, the method further comprises operatively coupling the hand engagement member to an anchor using an attachment member. In some such embodiments, operatively coupling comprises tethering.

In some embodiments, the method further comprises applying an attachment force to urge the hand engagement member into a non-engaged position when the hand engagement member is disengaged from the hand of the user.

In some embodiments, the hand engagement member is configured to move from a first engaged position to a second engaged position when the force is applied by the force application mechanism.

In some embodiments, when the hand engagement member is moved from the first engaged position to the second engaged position, the hand engagement member causes the hand to rotate or move in an arcuate range of motion substantially about a longitudinal axis of an arm of the user. In some such embodiments, when the hand engagement member is moved from the first engaged position to the second engaged position, the hand engagement member allows the hand to move in a natural range of motion as the arm is pronated or supinated.

BRIEF DESCRIPTION OF THE DRAWINGS

Figure 1:
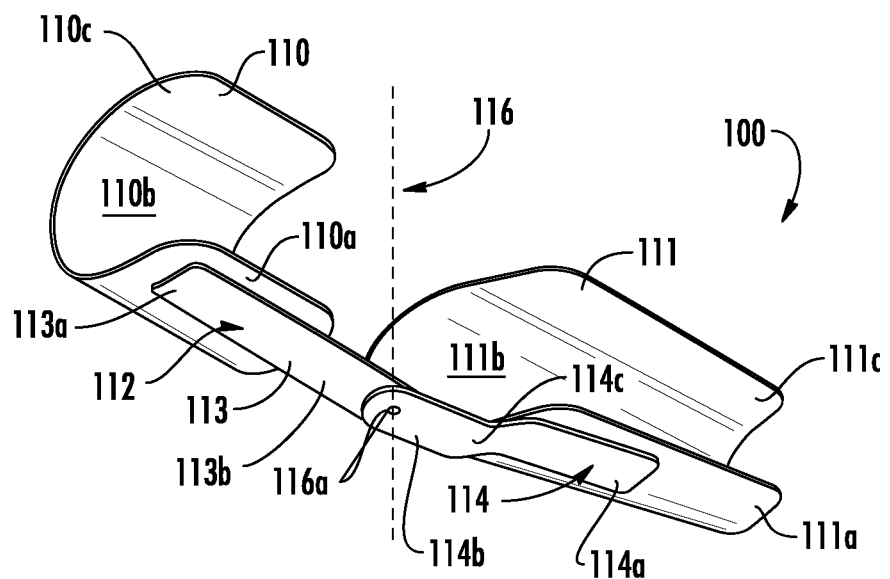
Figure 2:
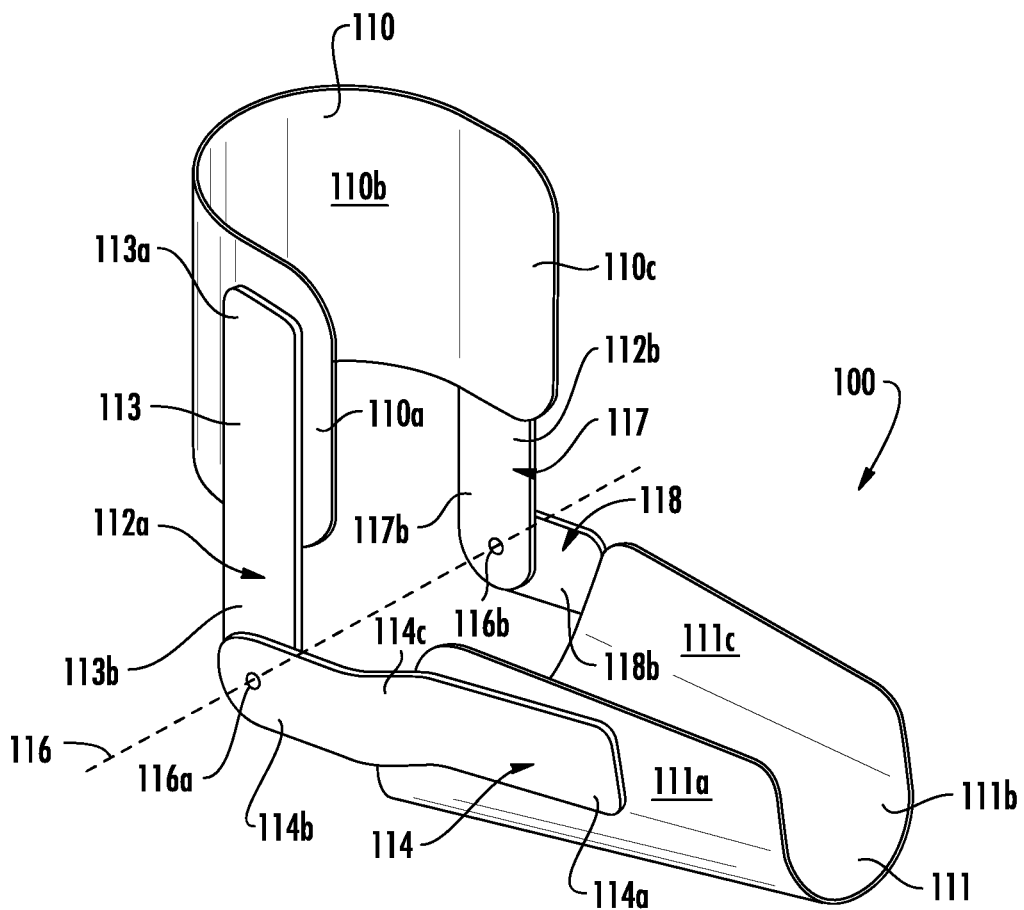
Figure 3:
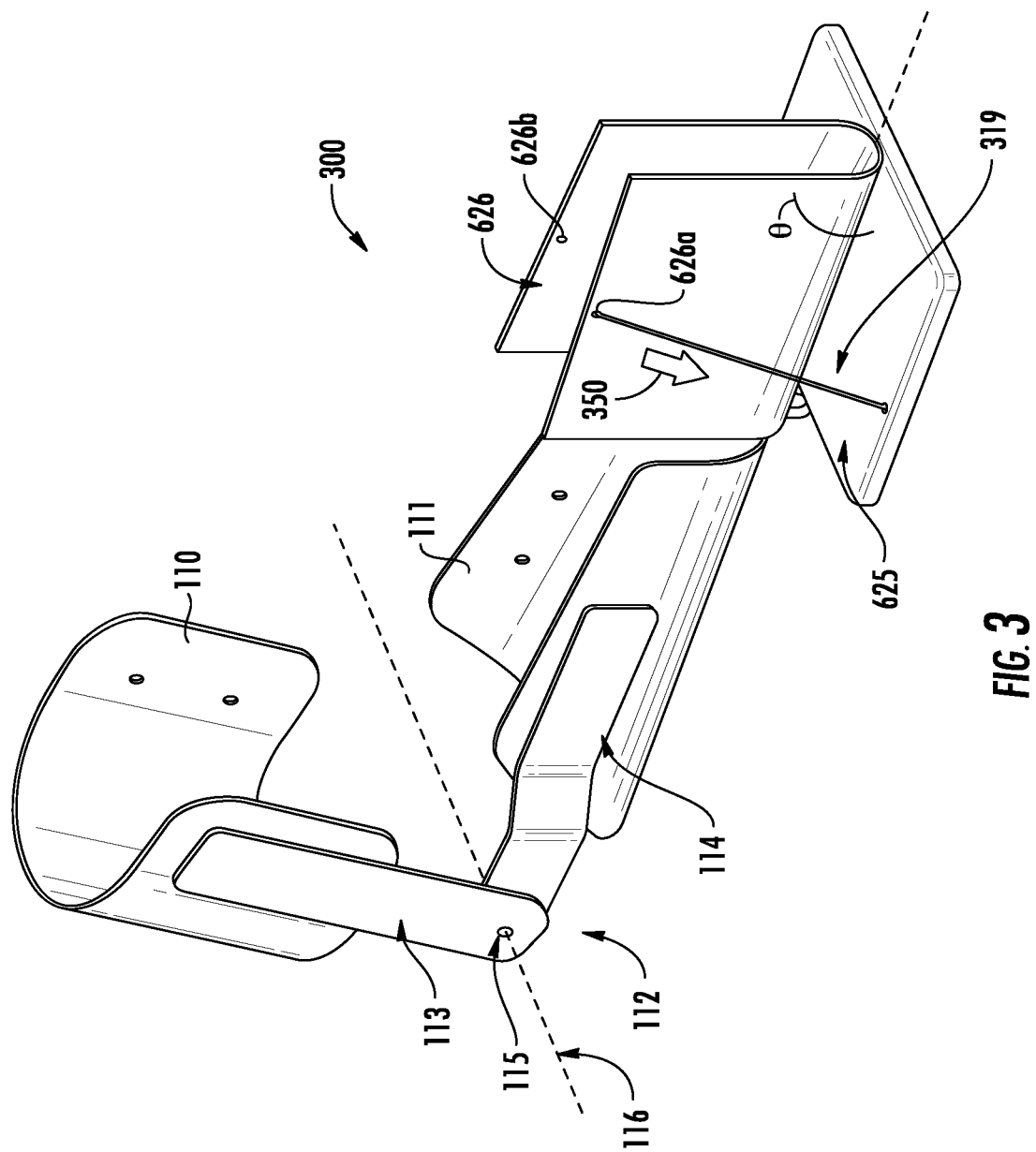
Figure 4:
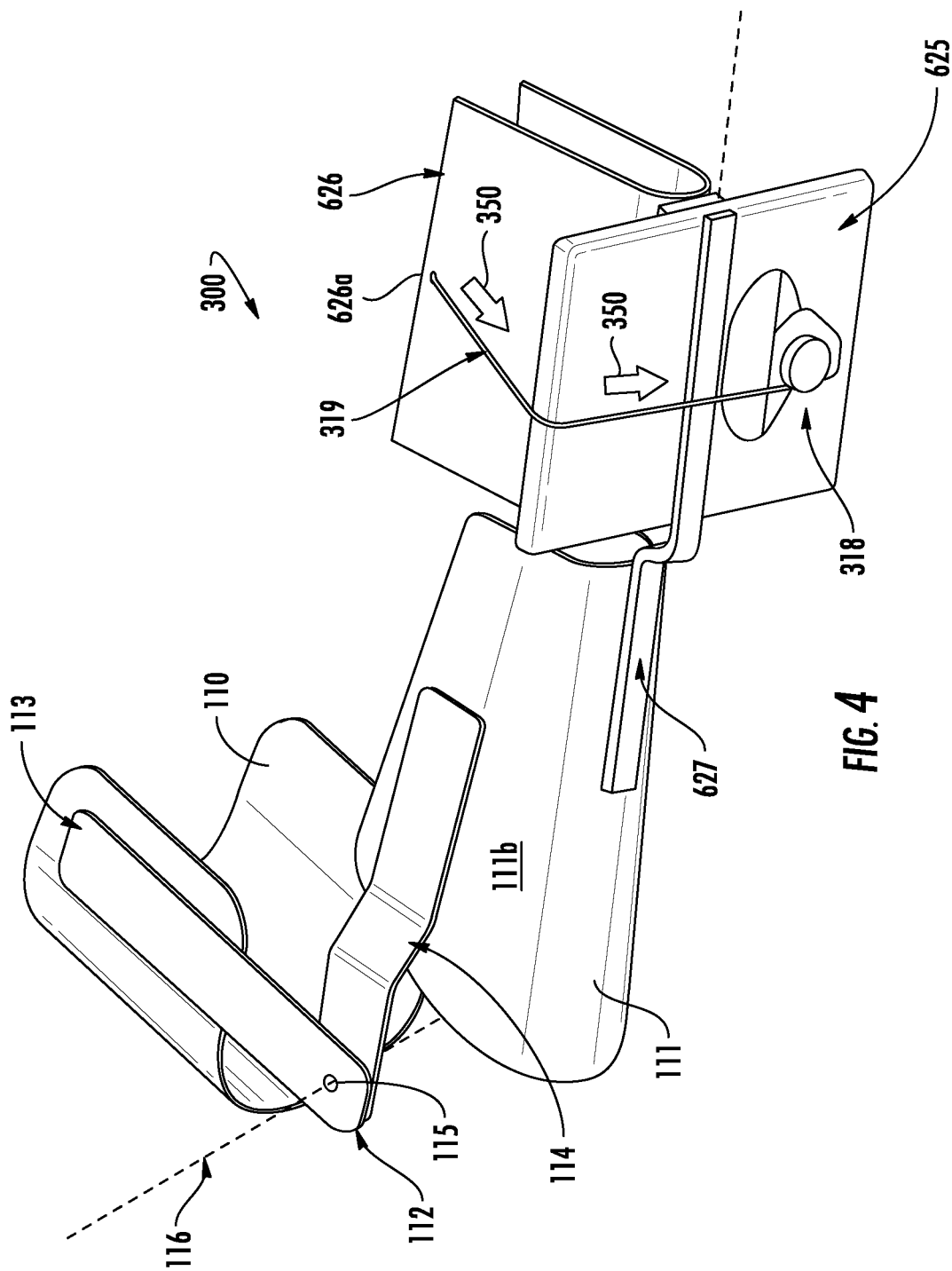
Figure 5:
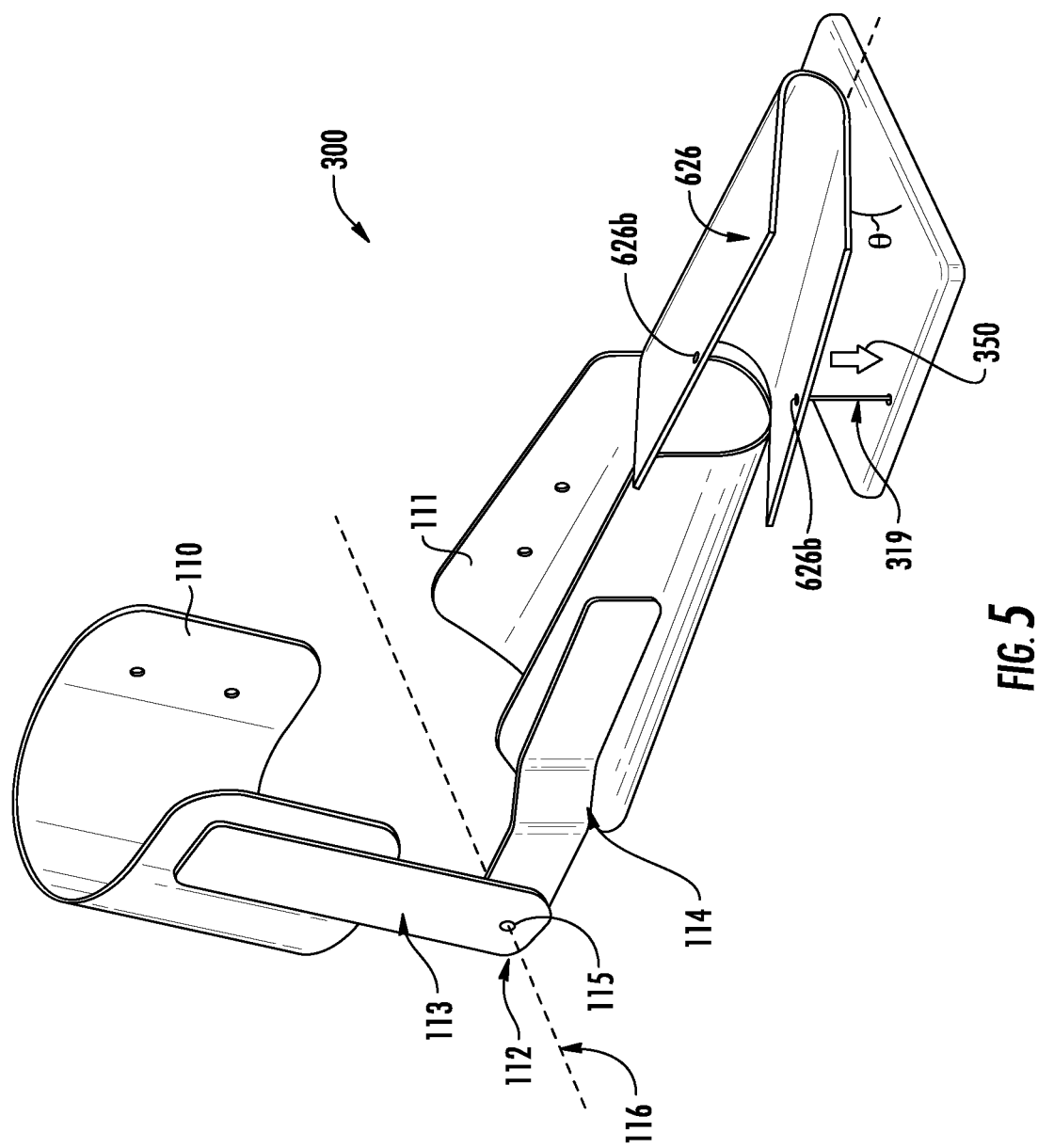
Figure 6:
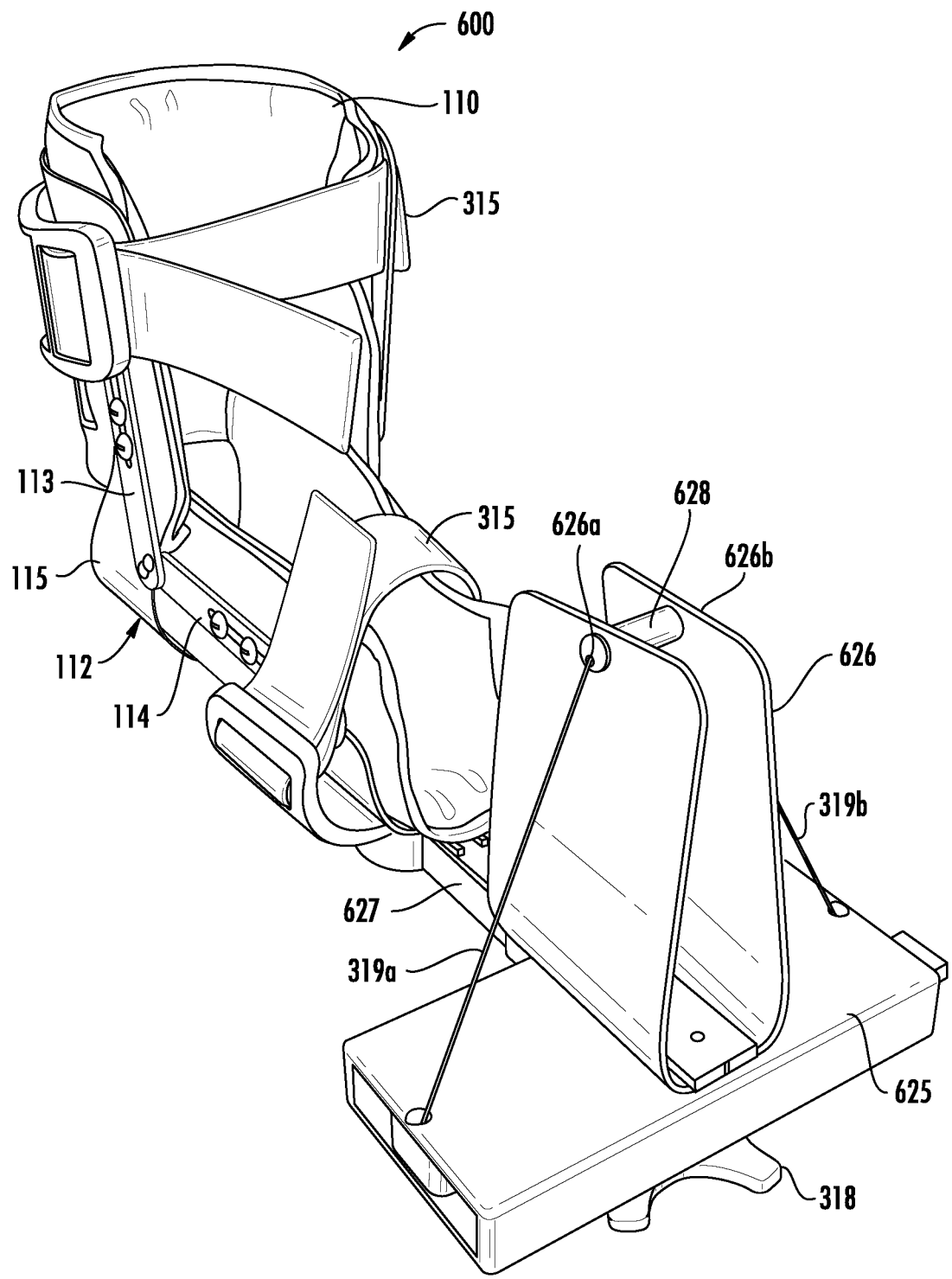
Figure 7A:
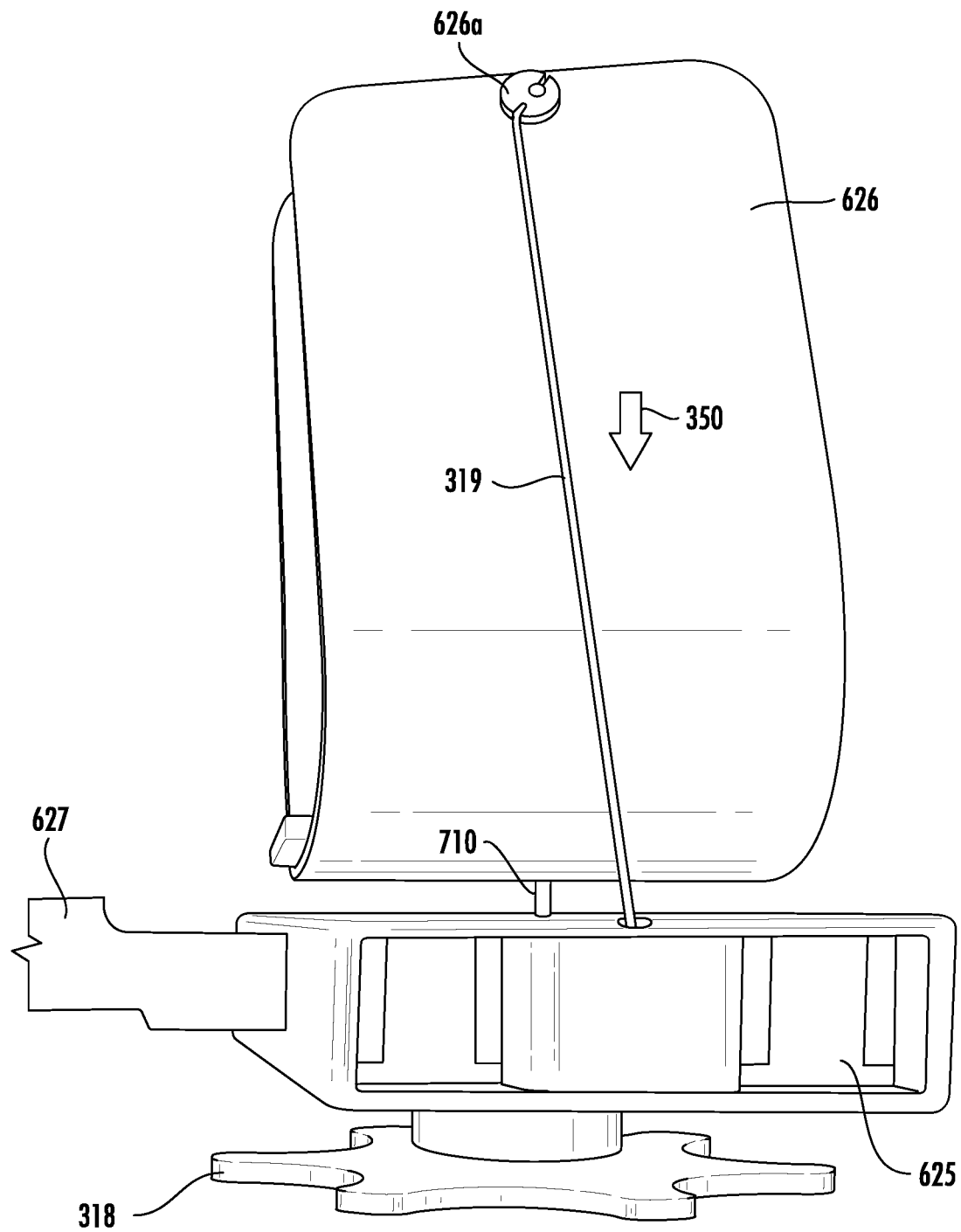
Figure 7B:
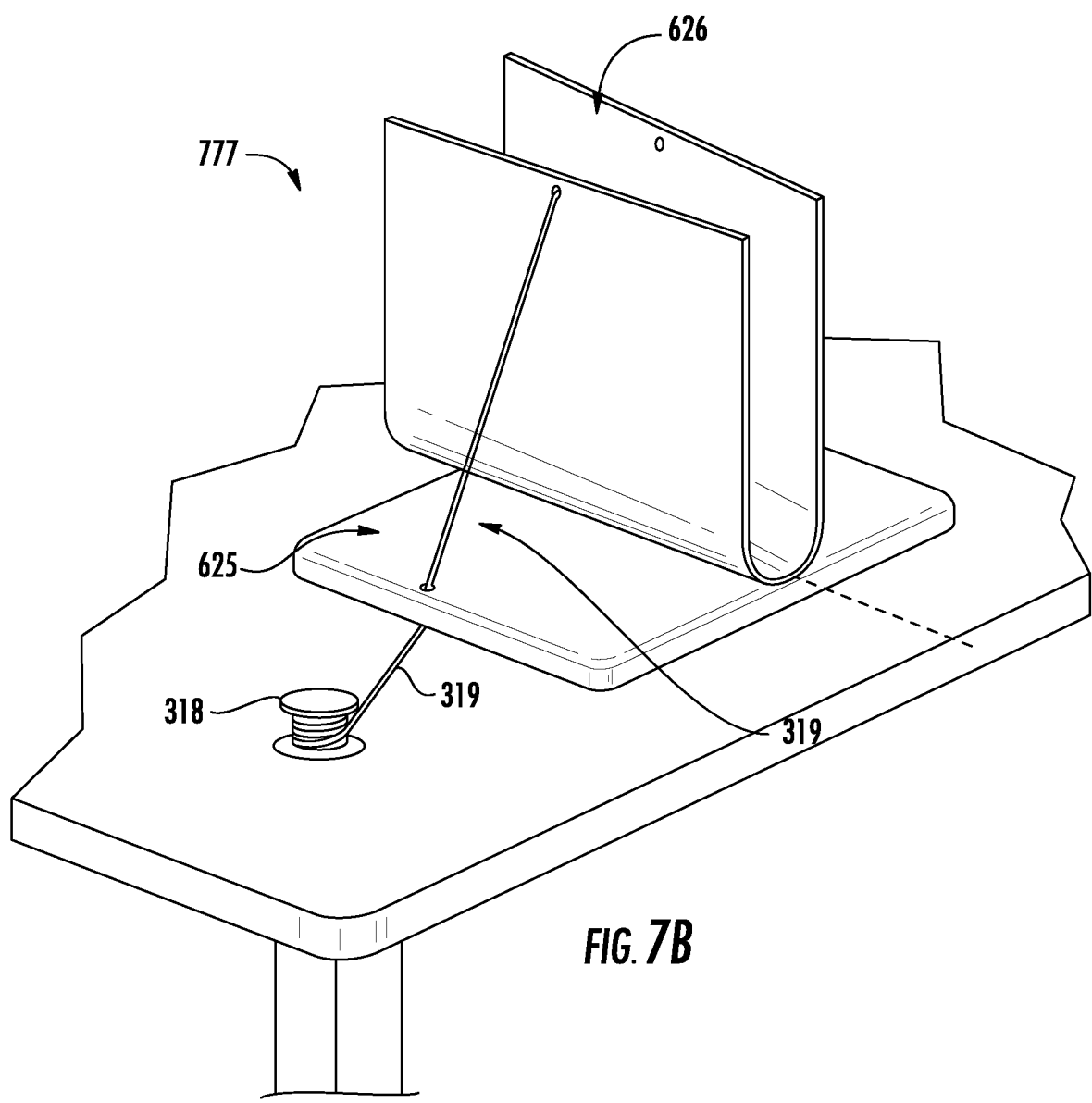

Having thus described embodiments of the invention in general terms, reference will now be made to the accompanying drawings, where:

FIG. 1 is a diagram illustrating an upper extremity support and range of motion device in accordance with embodiments of the present invention;

FIG. 2 is a diagram illustrating an upper extremity support and range of motion device in accordance with embodiments of the present invention;

FIG. 3 is a diagram illustrating a device for assisting with pronation and/or supination in accordance with embodiments of the present invention;

FIG. 4 is a diagram illustrating a device for assisting with pronation and/or supination in accordance with embodiments of the present invention;

FIG. 5 is a diagram illustrating a device for assisting with pronation and/or supination in accordance with embodiments of the present invention;

FIG. 6 is a diagram illustrating a device for assisting with pronation and/or supination in accordance with embodiments of the present invention;

FIGS. 7A and 7B are diagrams illustrating devices for assisting with pronation and/or supination in accordance with embodiments of the present invention;

FIGS. 8A-8G are diagrams illustrating a force application mechanism in accordance with embodiments of the present invention;

FIGS. 9A-9F are diagrams illustrating a force application mechanism in accordance with embodiments of the present invention;

FIGS. 10A-10H are diagrams illustrating a force application mechanism in accordance with embodiments of the present invention;

FIG. 11A-11E are diagrams illustrating a force application mechanism are diagrams illustrating a force application mechanism in accordance with embodiments of the present invention; and FIG. 12 is a flowchart illustrating a method for manipulating a hand of a user to provide pronation and/or supination assistance according to embodiments of the invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

To optimally treat a loss of motion within a joint, various embodiments of the invention may provide support to the joint and/or are capable of providing the necessary force to stretch scar tissue, thus returning the joint to its full range of motion. Devices that solely provide support to the joint only allow for uninterrupted healing of the joint which likely does not return the joint to the range of motion required by the patient.

Referring now to FIG. 1, an upper extremity support and range of motion device 100 is illustrated according to one embodiment of the present invention. It should be noted that as used herein the upper extremity support and range of motion device may be simply referred to as "the device". As shown in FIG. 1, the device 100 is defined by an upper extremity support structure that generally comprises an upper arm support member 110, a forearm support member 111, and at least one hinge assembly 112 operatively coupled to the support members 110, 111. The at least one hinge assembly 112, in some embodiments, comprises two hinge plates 113, 114 attached to one another at an articulated joint 115 such that an upper hinge plate 113, and a lower hinge plate 114 pivot with respect to a first axis 116. As illustrated in FIG. 2, in some embodiments, the device 100 may comprise two hinge assemblies 112a, 112b positioned parallel to one another on opposite sides of the upper arm support member 110 and the forearm support member 111.

In one embodiment, the device is positioned with respect to a joint (e.g., elbow joint) of an individual wearing the device (hereinafter, the "wearer" or the "user") such that the upper arm support member 110 and the forearm support member 111 are attached to the upper arm and forearm of the user, respectively, and the first axis 116 is parallel to a pivoting axis of the respective body part (e.g., the elbow). In exemplary embodiments, after the upper arm support member 110 and the forearm support member 111 have been suitably attached to the user's arm, the arm can bend at the elbow as the various members pivot relative to the first axis 116.

Referring again to FIG. 1, FIG. 1 illustrates a side oblique view of the upper extremity support and range of motion device 100. The device may be formed of various materials, including but not limited to a rigid plastic, wood metal, or other suitable materials such as any other erect material that provides needed support. It should be noted that the material of the device may vary based on the device component being constructed or the function of the device component. For example, the upper arm support member 110 and the forearm support member 111 may be constructed from a rigid plastic, and the hinge assembly 112 may be constructed from a metal. It should be understood that FIG. 1 may represent a simplified version of some embodiments of the invention. Padding of the upper arm support member 110 and forearm support member 111 may be optionally used if desired to increase comfort for the wearer. A plurality of straps or other attachment means may also be used as a method of securing the upper extremity support and range of motion device 100 to the wearer.

The upper arm support member 110 and forearm support member 111 may utilize a cradle and/or cuff configuration. As shown in FIG. 1, in one embodiment, a first end 113a of the upper hinge plate 113 is operatively coupled to the exterior of the upper arm support member 110, proximate to the edge of a first end 110a of the upper arm support member 110, such that the hinge plate 113 is parallel or generally parallel to the first end 110a of the upper arm support member 110, and the hinge plate extends outward from the upper arm support member 110 towards the lower hinge plate 114. As used herein, the phrase "proximate to an edge" may refer to a position that is either near and/or on the edge. In other embodiments of the invention, the upper hinge plate 113 may be operatively coupled to an interior surface of the upper arm support member 110 or in between two or more layers of an upper arm support member 110. The first end 110a of the upper arm support member 110 extends away from the upper hinge plate 113 into a medial portion 110b of the upper arm support member such that the medial portion 110b of the upper arm support member 110 is positioned substantially beneath the upper hinge plate 113, and a second end 110c of the upper arm support member 110 is parallel to the first end 110a of the upper arm support member 110.

Likewise, in the embodiment of FIG. 1, a first end 114a of the lower hinge plate 114 is operatively coupled to the exterior of the forearm arm support member 111, proximate to the edge of a first end 111a of the forearm support member 111, such that the lower hinge plate 114 is parallel to the first end 111a of the forearm support member 111, and the lower hinge plate 114 extends outward from the forearm support member 111 towards the upper hinge plate 113. In other embodiments of the invention, the lower hinge plate 14 may be operatively coupled to an interior surface of the forearm support member 111 or in between two or more layers of a forearm support member 111. The first end 111a of the forearm support member 111 extends away from the lower hinge 114 into a medial portion 111b of the forearm support member such that the medial portion 111b of the forearm support member 111 is positioned substantially beneath the lower hinge 114, and a second end 111c of the forearm support member 111 is parallel to the first end 111a of the forearm support member 110. The upper hinge plate 113 is operatively coupled to the upper arm support member 110 and the lower hinge plate 114 is operatively coupled to the forearm support member 111. As used herein, operatively coupled may be refer to two or more members being permanently or removably coupled to one another in either a fixed and/or movable position.

Furthermore, in the embodiment of FIG. 1, the upper hinge plate 113 and the lower hinge plate 114 may be operatively coupled to one another at a joint location 116a located relative to the first axis 116 (configured to align generally with the elbow joint of the wearer, in some embodiments) such that the first axis 116 extends through the joint location 116a. The joint location 116a may be defined by apertures located within the ends 113b, 114b of the upper hinge plate 113 and the lower hinge plate 114, respectively. In such an embodiment, the upper hinge plate 113 and the lower hinge plate 114 may be operatively coupled to one another at the joint location 116a using one or more coupling mechanisms including, but not limited to, nuts, bolts, screws, adhesive, rivets, pins, dowels, and the like. In one embodiment, the upper hinge plate 113 is defined by a flat plate, where the first end 113a of the upper hinge plate 113 is further defined by a squared end shape, and the second end 113b of the upper hinge plate 113 is further defined by a rounded end shape. The lower hinge plate 114, in some embodiments, is defined by angled plate, where the first end 114a of the lower hinge plate 114 is further defined by a squared shape, the second end 114b of the lower hinge plate is further defined by a rounded shape, and a medial portion 114c of the lower hinge plate 114 extends outward and/or downward at an obtuse angle with respect to the first end 111a of the forearm support member 111 towards the second end 114b of the lower hinge plate 114. In another embodiment, the medial portion 114c of the lower hinge plate 114 extends inward and/or upward at an angle with respect to the first end 111a of the forearm support member 111 towards the second end 114b of the lower hinge plate 114.

Referring again to FIG. 2, as previously mentioned FIG. 2 illustrates the use of a possible second hinge assembly along the first axis 116 to provide added stability and protection for the patient while wearing the upper extremity support structure. As such, the embodiments discussed herein may utilize either a single or double hinge assembly configuration. As shown in FIG. 2, in one embodiment, a first end 113a of the first upper hinge plate 113 is operatively coupled to the exterior of the upper arm support member 110, proximate to the edge of a first end 110a of the upper arm support member 110, such that the first upper hinge plate 113 is parallel to the first end 110a of the upper arm support member 110, and the first upper hinge plate 113 extends from the upper arm support member 110 towards a first lower hinge plate 114. The first end 110a of the upper arm support member 110 extends away from the first upper hinge plate 113 into a medial portion 110b of the upper arm support member such that the medial portion 110b of the upper arm support member 110 is positioned substantially beneath the first and second upper hinge plates 113, 117 respectively. A second end 110c of the upper arm support member 110 is parallel to the first end 110a of the upper arm support member 110, and the second upper hinge plate 117 is operatively coupled to the exterior of the upper arm support member 110, proximate to the edge of a second end 110c of the upper arm support member 110 such that the second upper hinge plate 117 is parallel to the second end 110c of the upper arm support member 110. As previously discussed the first and second upper hinge plates 113, 117 may be operatively coupled to an interior surface or within one or more layers of the upper arm support 110.

Likewise, in the embodiment of FIG. 1, a first end 114a of the lower hinge plate 114 is operatively coupled to the exterior of the forearm support member 111, proximate to the edge of a first end 111a of the forearm support member 111, such that the first lower hinge plate 114 is parallel to the first end 111a of the forearm support member 111, and the first lower hinge plate 114 extends from the forearm support member 111 towards a first upper hinge plate 113. The first end 111a of the lower arm support member 111 extends away from the first lower hinge plate 114 into a medial portion 111b of the forearm support member 111 such that the medial portion 111b of the forearm support member 111 is positioned substantially beneath the first and second lower hinge plates 114, 118 respectively. A second end 111c of the forearm support member 111 is parallel to the first end 111a of the forearm support member 111, and the second lower hinge plate 118 is operatively coupled to the exterior of the forearm support member 111, proximate to the edge of a second end 111c of the forearm support member 111 such that the second lower hinge plate 118 is parallel to the second end 111c of the forearm support member 111. As previously discussed the first and second lower hinge plates 114, 118 may be operatively coupled to an interior surface or within one or more layers of the forearm support member 111.

Furthermore, in the embodiment of FIG. 2, the second upper hinge plate 117 and the second lower hinge plate 118 may be operatively coupled to one another at a joint location 116b located relative to the first axis 116 (configured to align generally with the elbow joint of the wearer, in one embodiment) such that the first axis 116 extends through the joint location 116b. The joint location 116b may be defined by apertures located within the ends 117b, 118b of the second upper hinge plate 117 and the second lower hinge plate 118, respectively. In such an embodiment, the upper hinge plate 113 and the lower hinge plate 114 may be operatively coupled to one another at the joint location 116b using one or more coupling mechanisms as previously discussed herein. In one embodiment, the second upper hinge plate 117 is defined by a flat plate, where the first end 117a of the upper hinge plate 117 is further defined by a squared shape, and the second end 117b of the upper hinge plate 117 is further defined by a rounded shape. The second lower hinge plate 118 is defined by angled plate, where the first end 118a of the lower hinge plate 118 is further defined by a squared end shape, the second end 118b of the lower hinge plate is further defined by a rounded end shape, and a medial portion 118c of the lower hinge plate 118 extends outward and/or downward at an angle with respect to the first end of the forearm support member 111a towards the second end 118b of the lower hinge plate 118.

Apparatus for Providing Pronation and Supination of the Forearm/Wrist

The following embodiments and additional components may be discussed in conjunction with the embodiments of FIGS. 1 and 2 for the purpose of providing pronation and supination of the forearm/wrist. As such, FIG. 3 through FIG. 7B shows the device 100 in more detail than previously depicted in FIG. 1 and FIG. 2. FIG. 3 through FIG. 7B illustrates some possible variations of the apparatus aimed at further promoting pronation/supination of the forearm/wrist/hand. Pronation/supination is commonly defined as a rotation of the forearm along the longitudinal axis of the forearm. Pronation and supination are opposite movements; an example of pronation is rotation of the forearm that moves the palm from an anterior-facing position to a posterior facing position, or palm facing down. An example of supination is the opposite movement—moving the palm from a relatively posterior facing position to an anterior-facing position, or palm facing up.

The basis of embodiments of the invention is a device having a hand engagement member 626, an anchor 625, a force applicator 319, and a force application mechanism 318, configured to manipulate a forearm of a user 314 into pronation or supination when the force application mechanism 318 applies a force 350 to the hand engagement member 626, relative to the anchor 625, via the force applicator 319. The force applicator 319 may further comprise a member portion and an anchor portion. For example, the member portion may be a first end of a cable attached to a device member, and the anchor portion may be a second end of a cable attached to a device anchor. One embodiment of the invention comprises the anchor 625 being operatively coupled to the general device 100 shown in FIGS. 1 and 2, or another arm brace device. Another embodiment of the invention comprises the anchor 625 being operatively coupled to any solid surface and does not require the anchor 625 and hand engagement member 626 assembly to be attached to an arm brace of any kind.

In one embodiment, the user of the configuration shown in FIG. 3 may affix the device 100 to their upper arm and forearm and place their hand inside the "U"-shaped (or taco-shell-shaped) cavity defined within the hand engagement member 626. The force application mechanism 318 may then be utilized to pull the hand engagement member 626, via the force applicator 319, towards the anchor 625 and thus promote one of either pronation or supination, depending on the selected device configuration setting. In some embodiments, the force applicator 319 may be and/or include a cable, belt, line, elastic band, inelastic band, chain, wire, ribbon, some combination of the foregoing, and/or the like.

The force applicator 319 may be routed around the anchor 625 and operatively coupled attach to either (or both) of the top edges (or proximate either of the top edges) of the hand engagement member 626, depending on the type of movement desired. In one embodiment, the force applicator 319 may attach to the edge that is opposite of the side from which it was routed. For example, the force applicator 319 may be routed from the left side of the hand engagement member 626 and may attach to the top edge of the right sides of the hand engagement member 626. Likewise, the force applicator 319 may be routed from the right side of the hand engagement member 626 and may attach to the top edge of the left sides of the hand engagement member 626. In this way, the force applicator 319 may cross from two sides of the hand engagement member 626 and apply force from opposite sides of the hand engagement member 626. In another embodiment, this connection may be accomplished by use of at least one of apertures 626a and/or 626b in the hand engagement member 626. As an example, if the right arm was placed in the device 300 shown in FIGS. 3-5, and the force applicator 319 was configured as shown, attaching to aperture 626a, the right forearm would experience supination upon activation of the force application mechanism 318. If the force applicator 319 was reconfigured such that the force applicator 319 was attached to aperture 626b instead, the right forearm would experience pronation upon activation of the force application mechanism 318. In other embodiments of the invention, other means of operatively coupling the force applicator 319 to the hand engagement member 629 may include a force applicator support member molded into, glued, or otherwise operatively coupled to the hand engagement member 629 or other like coupling means.

In one configuration, the anchor 625 may contain guides on the sides of the anchor 625, in the form of apertures, hooks, or another feature that is capable of allowing a force applicator 319, like a cable, to pass by or through without allowing the force applicator 319 to slip away from the designed configuration.

FIG. 3 shows the device 300 in an unengaged position, where the hand engagement member 626 is disengaged from a hand of the user. As used herein, disengagement may refer to not engaging a component of body member such as the hand of a user. The user may engage the device 300 by placing the hand of the user within the U-shaped receptacle formed by the hand engagement member 626 such that the hand engagement member 626 engages at least a portion of the palmar side of the hand, at least a portion of the dorsal side of the hand, and/or at least a portion of the ulnar side of the hand of the user. In some embodiments, the hand engagement member is not U-shaped, but rather, merely consists of a single platform for engaging one of the palmar side of the hand or the dorsal side of the hand, or may include an opening with a cover or may include an enclosed opening such as oval shape though which a hand may be inserted to prevent the hand from slipping out of the hand engagement member 626. Once the hand of the user is engaged with the hand engagement member 626, the device 300 is in a first engaged position with an engagement plane substantially parallel with the frontal plane of the hand of the user. An angle $\theta$ is created between the engagement plane and the hand-facing surface of the anchor 625 while the device 300 is in the first engaged position. In some embodiments, the first engaged position is substantially similar to the position of the device 300 in FIG. 3, where the engagement plane is perpendicular to the hand-facing surface of the anchor 625. In another embodiment, the first engaged position may comprise the hand engagement member 626 lying flat on the hand-facing surface of the anchor 625, such that the engagement plane may be substantially parallel to the hand-facing surface of the anchor 625. In other embodiments, the first engaged position may be anywhere within the range of angles from a fully pronate to fully supinated.

Continuing with the illustration of FIG. 3, as the force application mechanism 318 is activated; the force applicator 319 is shortened and thereby provides a force 350 on the hand engagement member 626, causing the hand to rotate substantially about the longitudinal axis of the arm 216. If a user was engaging the hand engagement member 626 with the right hand of the user, then the user's right arm would be entering supination as the force 350 is applied to the hand engagement member 626. FIG. 5 illustrates a second engaged position, which is a result of applying the force 350 to the hand engagement member 626. As the force applicator 319 is shortened, the top edge of the hand engagement member 626, specifically the connection or aperture 626a, is drawn toward the anchor 625. Simultaneously, the angle $\theta'$ between the engagement plane and the hand-facing surface of the anchor 625 is decreased, or becomes more acute. The smaller, or more acute, angle $\theta'$ is, the greater the pronation or supination, depending on the hand's orientation. For example, if a user's right hand was engaged with the device 300 as shown in FIG. 5, the user's right hand would be in substantial supination. Alternatively, if the user's left hand was engaged with the device 300 as shown in FIG. 5, the user's left hand would be in substantial pronation. It should be noted that in some embodiments, angle θ' may be greater than angle θ, such that the second engaged position is in a less pronated or supinated state than the first engaged position. Similarly, it should be noted that a user's hand may require supination or pronation assistance at any angle greater than zero including any angle greater than ninety degrees (with respect to the hand-facing surface of the anchor).

Referring to FIG. 4, an attachment member 627 may be centrally positioned on and/or operatively coupled to the bottom of the medial portion 111b of the forearm support member 111 such that the attachment member 627 extends outward from the forearm support member 111 towards the hand engagement member 626. The attachment member 627 may be further operatively coupled to the anchor 625 at one or more joint locations such that the anchor 625 is positioned above at least a portion of the attachment member 627 that extends beyond the edge front edge of the forearm support member 111, and the force application mechanism 318 is positioned adjacent to at least a portion of the attachment member 627 that extends beyond the front edge of the forearm support member 111.

One configuration of the device 600, illustrated in FIG. 6, comprises a force application mechanism 318 with two activation modes and two force applicators 319a, 319b. The ends of such force applicators 319a, 319b would be attached to their respective apertures 626a, 626b in the hand engagement member 626. In such an embodiment, the first activation mode of the force application mechanism 318 may cause the first force applicator 319a to retract and cause or allow the second force applicator 319b to extend. In this configuration, activating the force application mechanism 318 would manipulate a wearer's right arm into supination. Continuing the example, switching the activation mode of the force application mechanism 318 may then cause the second force applicator 319b to retract and cause or allow the first force applicator 319a to extend. In this configuration, activating the force application mechanism 318 would manipulate a wearer's right arm into pronation. Therefore, the device 600 does not need to be reconfigured to switch from manipulating an arm in pronation to supination and vice versa.

In one embodiment the dual activation mode configuration of the force application mechanism 318 would be accomplished by using a rotating dial as the force application mechanism 318, where rotating the dial in one direction provides a force on the force applicator 319a, and rotating the dial in the opposite direction provides a force on the force applicator 319b. In one embodiment, two force application mechanisms may be provided such that one force application mechanism applies a force through one force applicator and the other force application mechanism applies a force through a second force applicator, in an opposite rotational direction. In some embodiments of the invention, the force application mechanism 318 is located on the bottom of the anchor 625. In other embodiments, the force application mechanism 318 is located on a support of the brace device 100. In another embodiment, the force application mechanism 318 may be located external to the device 600 in general.

Still referring to FIG. 6, in an alternate embodiment, the force application mechanism 318 may be positioned on the bottom of the anchor 625. The force applicator 319 may extend outward from both sides of the force application mechanism 318 such that it extends alongside the bottom of the anchor 625 toward the top of the hand engagement member 626, and further extend through the interior of a hand engagement member connector 628 operatively attached to two apertures 626a, 626b within the top of the hand engagement member 626 using one or more coupling mechanisms including, but not limited to, nuts, bolts, screws, adhesive, other rivets, and the like. In such an embodiment, the force applicator 319 may form a substantially triangular configuration with respect to the hand engagement member 626 and the anchor 625.

FIG. 7A illustrates one embodiment of the anchor 625 and hand engagement member 626 assembly, in which the bottom of the hand engagement member 626 may be operatively coupled to the anchor 625 by an attachment member 710. The illustrated embodiment in FIG. 7A shows the hand engagement member 626 lifted above the anchor 625, but this is for illustrative purposes only. When the hand engagement member 626 is not engaged by the hand, the hand engagement member 626 generally may rest atop the anchor 625. In other embodiments the hand engagement member 626 may be located at least partially off of the anchor 625 by a spacer. When the hand engagement member 626 is resting on the anchor 625, the attachment member 710 may either be positioned between the hand engagement member 626 and the anchor 625, extend into the anchor 625, and/or extend into the hand engagement member 626.

In one embodiment of the invention, the hand engagement member 626 may be pivotally connected to the hand-facing side of the anchor 625. In such an embodiment, one or more hinges may secure the base of the hand engagement member 626 to the anchor 625 such that the hand engagement member 625 may rotate around the axis of the one or more hinges. Hinging the hand engagement member 626 to the anchor 625 has the effect of causing the forearm and hand of a user to follow an arched path around the axis defined by the hinges, with the dorsal side of the user's hand staying in close proximity to the hinge axis.

FIG. 7A is a close-up view of an alternative embodiment of device 300 wherein the hand engagement member 626 may be operatively connected to the anchor 625 by a non-hinge attachment member 710, such as a tether, track, groove, magnet, and/or the like. For example a first track may extend from the hand engagement member 626, and a second track may extend from the anchor 625, where the track may be operatively coupled via corresponding grooves within the tracks. In another example, the attachment member 710 may be attached at one end to the hand engagement member 626, and at the other end to the anchor, via an aperture, hook, glue, or other adhesive method. The attachment member 710 may be embodied as an elastic material capable of maintaining the hand engagement member 626 in an upright position, relative to the anchor 625, through a small force on the hand engagement member, when the device 100 is in an unengaged position. In such an embodiment, the force applied by the elastic member would not be significant enough to prevent the hand engagement member 626 from moving away from the anchor when engaged in pronation or supination. In another embodiment, the attachment member 710 may be embodied as an inelastic or elastic material that is in slack when the hand engagement member 626 is resting on, proximate to or substantially proximate to, the anchor 625, and wherein the operative connection applies a resistive or preventive force against the hand engagement member 626 when the hand engagement member 626 has moved a certain distance away from the anchor 625 such that the hand engagement member 626 may be allowed full pronation and/or supination rotation while not allowing a the hand engagement member 626 to slide substantially off of the anchor 625. In such embodiments, the hand engagement member 626 may be allowed to move freely along the anchor 625 so as to provide a "rocking" and/or sliding action atop the anchor 625.

In one embodiment, and as shown in FIG. 7A, the attachment member 710 is a single tether attached at the base of the U-shape of the hand engagement member 626. In this example embodiment, the attachment member 710 is an inelastic cord that recedes into the anchor 625 when the base of the hand engagement member 626 moves closer to the anchor 625 surface. Additionally, when the hand engagement member 626 moves a certain distance away from the attachment member's connection point to the anchor, the hand engagement member 626 is restricted from further movement in that direction by the restrictive force of the attachment member 710. In other embodiments of the invention the attachment member 710 may be a ball joint, with an opposing socket joint located in the anchor 625. The ball joint may allow for 360 degree rotation of the hand engagement member 626. In some embodiments of the invention, such as the tether or the ball joint may include stops that prevent the hand engagement member 626 from rotating more than a preset angle such as ninety degrees, or other like angle.

As illustrated in FIG. 7A, the hand engagement member 626 may separate completely from the anchor and is only restricted in movement by the attachment member 710 and the force applicator 319. Such an embodiment allows the hand engagement member 626 to move in all three dimensions, while staying parallel to the frontal plane of the hand of the user, and additionally allows the hand engagement member 626 to rotate along all three axes of motion: pitch, roll (pronation/supination), and yaw. The freedom of movement for the hand engagement member 626 that is provided in this embodiment allows a user's arm and hand to freely define its own, natural path or range of motion when undergoing pronation or supination. Such a freedom is not available with a hinged connection between the hand engagement member 626 and the anchor 625.

In one embodiment, the hand engagement member 626 and the anchor 625 are not connected at the base of the hand engagement member 626. In such an embodiment, the relatively flat bottom of the hand engagement member (shaped somewhat or substantially like a taco or taco shell) may freely slide, pivot, and rotate in relation to the anchor 625 without any securing means. Such absence of an attachment member 710 may allow a greater range of motion for the hand engagement member 626.

In one embodiment of the invention, the forearm support member 111 may be rotatable within the general frame of the device 100, such that as the forearm rotates in pronation or supination, the forearm support stays in contact with substantially the same parts of the forearm throughout the motion. In another embodiment, a supporting cuff may be located between the forearm support 111 and the forearm of the wearer such that the supporting cuff may rotate along with the forearm during pronation or supination. The benefit of either embodiment is to allow continued support of the forearm and provide comfort and stability to an arm that may have recently undergone surgery.

FIG. 7B illustrates one embodiment of the device 777 wherein the anchor 625 is not attached to a brace device 100, but is instead secured to a flat surface, such as a table or counter top. In such an embodiment, the hand engagement member 626 is still connected to the anchor 625 via an attachment member 710, and the hand engagement member is still attached to—and manipulated by—a force applicator 319. However, the force application mechanism 318 may be located in a position that is not directly underneath the anchor, such as off to the side, or attached to a side of the anchor. Continuing the example, the force applicator 319 will still be connected to the force application mechanism 318 and will still run through, or be guided along, the anchor 625. In such an embodiment, the device 1400 may still cause pronation or supination of an arm of a user, but the device 777 is not required to be attached to a brace or otherwise attached to the body of the user (other than where it engages the hand). This embodiment may allow further freedom of a user in using the device 777 because the elbow of the user is not restricted to a certain position relative to the anchor 625, as in some previously discussed embodiments.

In one embodiment, an incremental force may be applied to the device by the force application mechanism 318 and the force applicator 319. In such an embodiment, the force applicator 319 may be shortened in increments such that the force resulting from each increased increment, incrementally pivots the hand engagement member 625 about the axis 216 and, subsequently positions the hand/forearm of the wearer into pronation or supination. In one incremental force embodiment, the increments of force may be varied such that a larger increment may move the hand engagement member 626 in large steps of pronation/supination at first, and then provide a fine increment of force to adjust the hand engagement member 626 in small steps. Such an embodiment allows a wearer to quickly obtain a desired orientation of the hand and then apply a force in small steps to slowly rotate the forearm/hand in pronation or supination, stretching the tissue around a joint injury. In another embodiment, a continuous force may be applied to the hand engagement member 626 by the force application mechanism 318 and the force applicator 319. In such an embodiment, the force applicator 319 may be continuously shortened such that the resulting force continuously pivots the hand engagement member 626 about the axis 216 and, subsequently positions the hand/forearm of the wearer into pronation or supination. In either embodiment, the force may be applied in one direction with respect to the force application mechanism 318, and the force application mechanism 318 may comprise a means for releasing the force in an opposite direction (e.g., a release button) and subsequently lengthening the force applicator 319.

In one embodiment, the force application mechanism 318 is embodied by a dial ratchet, where a first end of the force applicator 319 is operatively coupled with the dial ratchet, the dial ratchet is operatively coupled to the end of the erect member 316, and a second end of the force applicator is operatively coupled to an aperture in the end of the erect member 317. In such an embodiment, the dial ratchet may be one directional such that in response to turning the dial counter clockwise, an incremental force is applied to the device, the force applicator 319 is incrementally shortened, the hinge assembly straightens and, subsequently the elbow of the wearer 314 is straightened or extended. In some embodiments, the dial may comprise a release that causes the dial to stop applying pressure and allow the elbow of the wearer 314 to pivot in both flexion and extension directions.

In various embodiments In one embodiment, as illustrated in FIGS. 8A through 8G, the force applicator mechanism 318 is embodied by a dial mechanism 800 having an upper dial member 800a, a lower dial member 800b, and a switch 800c where the upper dial member 800a rotates clockwise and/or counter-clockwise with respect to the lower dial member 800b, and the orientation of the switch 800c with respect to the upper dial member 800a allows for rotation of the upper dial member 800a in either two directions, or restricts the rotation of the upper dial member 800a to one (e.g., clockwise) direction.

The upper dial member 800a may comprise a plurality of plungers 802, rollers 804, springs 806, plates 808, or depressions 810. The bottom surface of the upper dial member 800a is defined by a spool 812 such that a force applicator 319 (e.g., a cable, a belt) may be wrapped around the spool 812, and may unravel and/or wind around the spool 812 to lengthen and/or shorten based on the orientation of the force applicator mechanism 318 (e.g., dial mechanism 800). The spool 812 may then be covered by the lower dial member 800b which may comprise an aperture 824 for allowing the force applicator 319 to exit the dial mechanism 800, a recess 822 in the top of the lower dial member 800b for receiving and being operatively coupled with the upper dial member 800a, and more specifically, the barrel 834 of the switch 800c. Furthermore, a recess 824 in the bottom of the lower dial member 800b may be internally threaded such that the dial mechanism 800 may be attached to another member (e.g., hinge plate) discussed previously herein. The switch 800c may comprise one or more pins 830, protrusions 832 located on the bottom surface switch 800c and a barrel 834 therein. The switch 800c may be operatively coupled with the upper dial member 800a. Specifically, the barrel 834 may be operatively coupled with the switch 800c via a fastener or rivet (e.g., a shoulder screw), or other like fastening means. The barrel 834 may then be securely positioned within an opening 816 in the center of the upper dial member 800a such that at least a portion 834a of the barrel 834 extends beyond the bottom surface of the upper dial member 800a, the extended portion 834a may be further shaped such that it securely fits within the recess 822 of the lower dial member. For example, as shown in the illustrated embodiments of FIG. 8, the extended portion 834a is square shaped such that is securely fits within the square shaped recess 822. In this way, the lower dial member 800b may be statically positioned such that, as the barrel 834 rotates, the upper dial member 800a dynamically moves with respect to the lower dial member 800b.

Figure 8A:
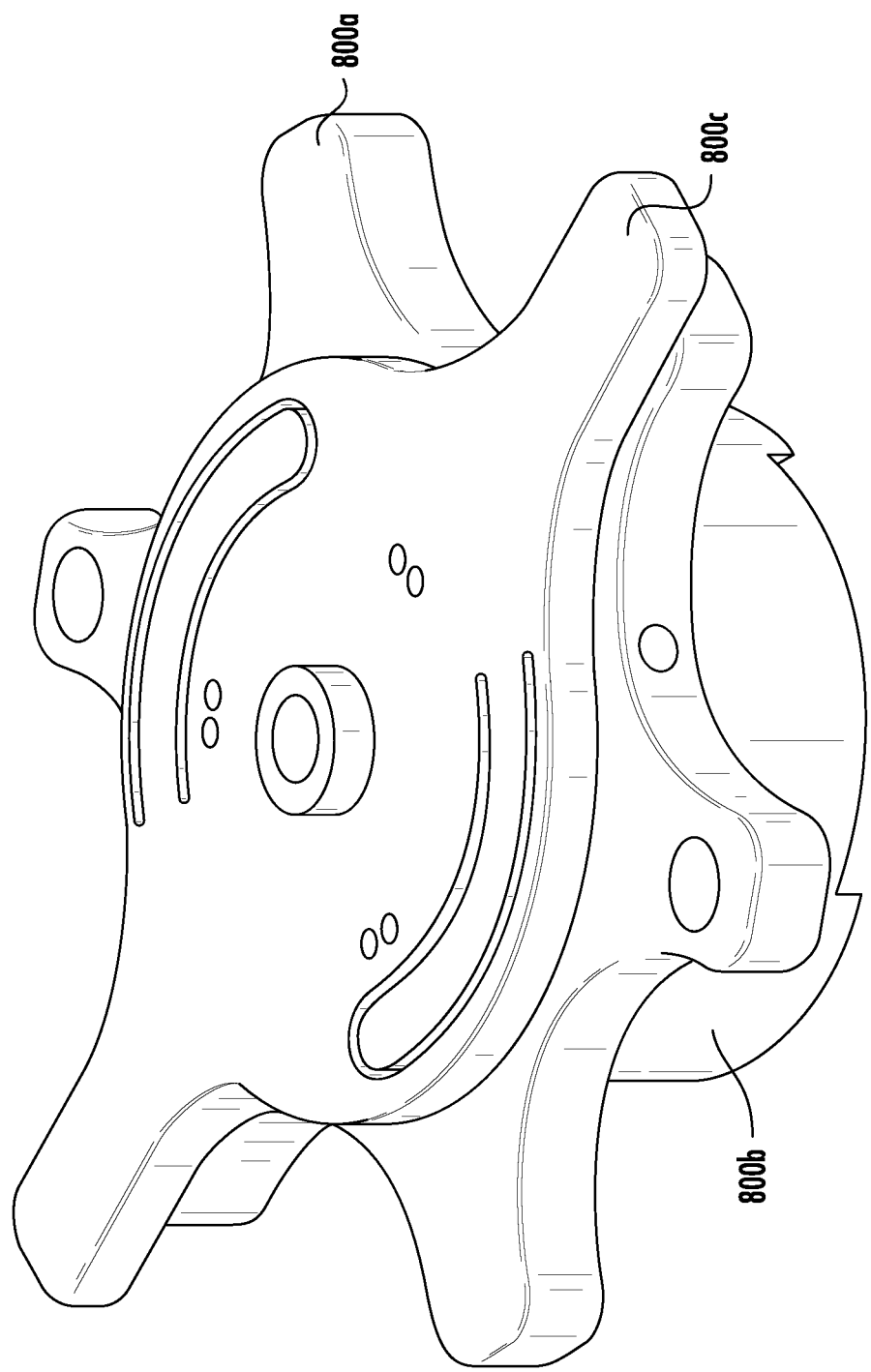
Figure 8B:
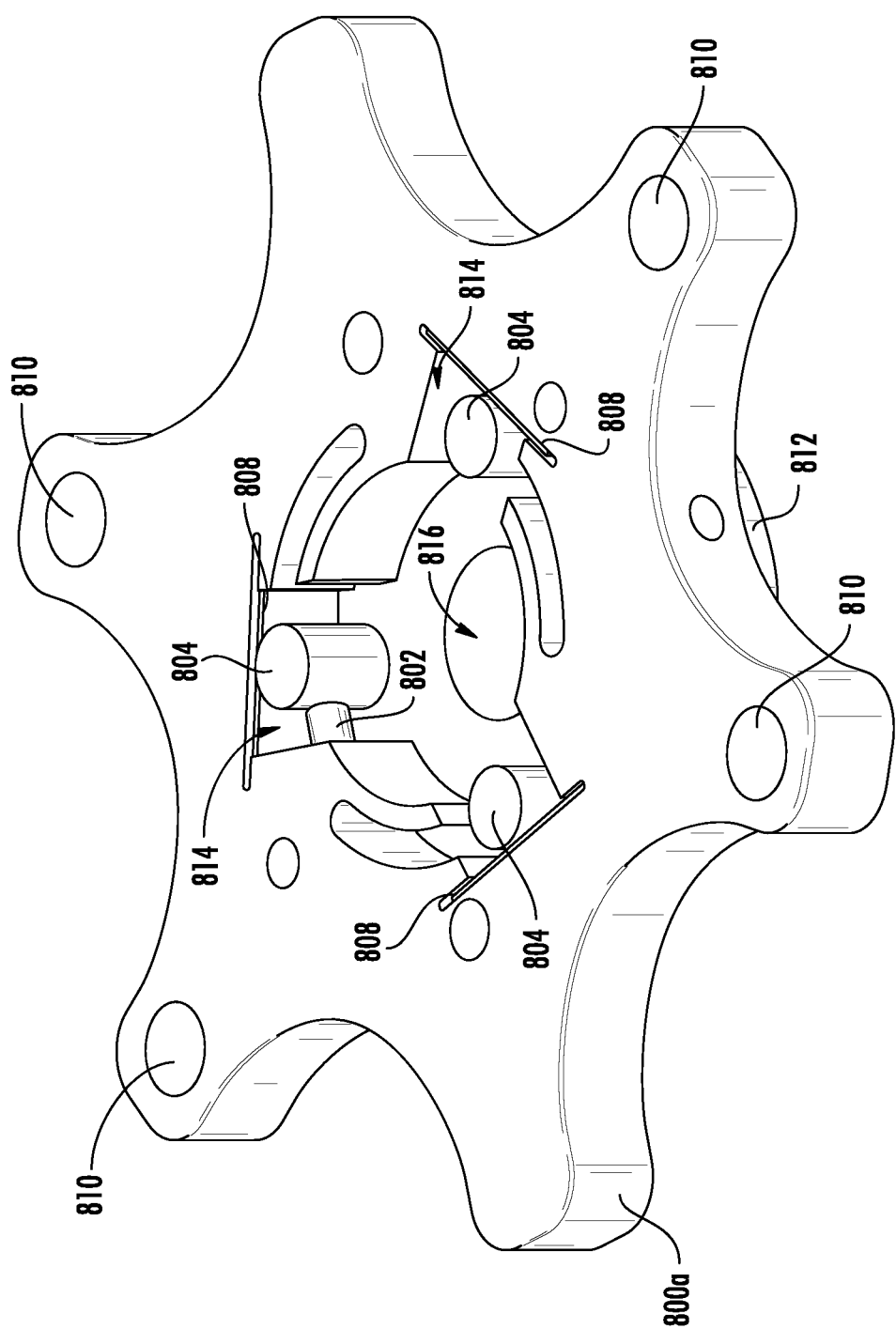
Figure 8C:
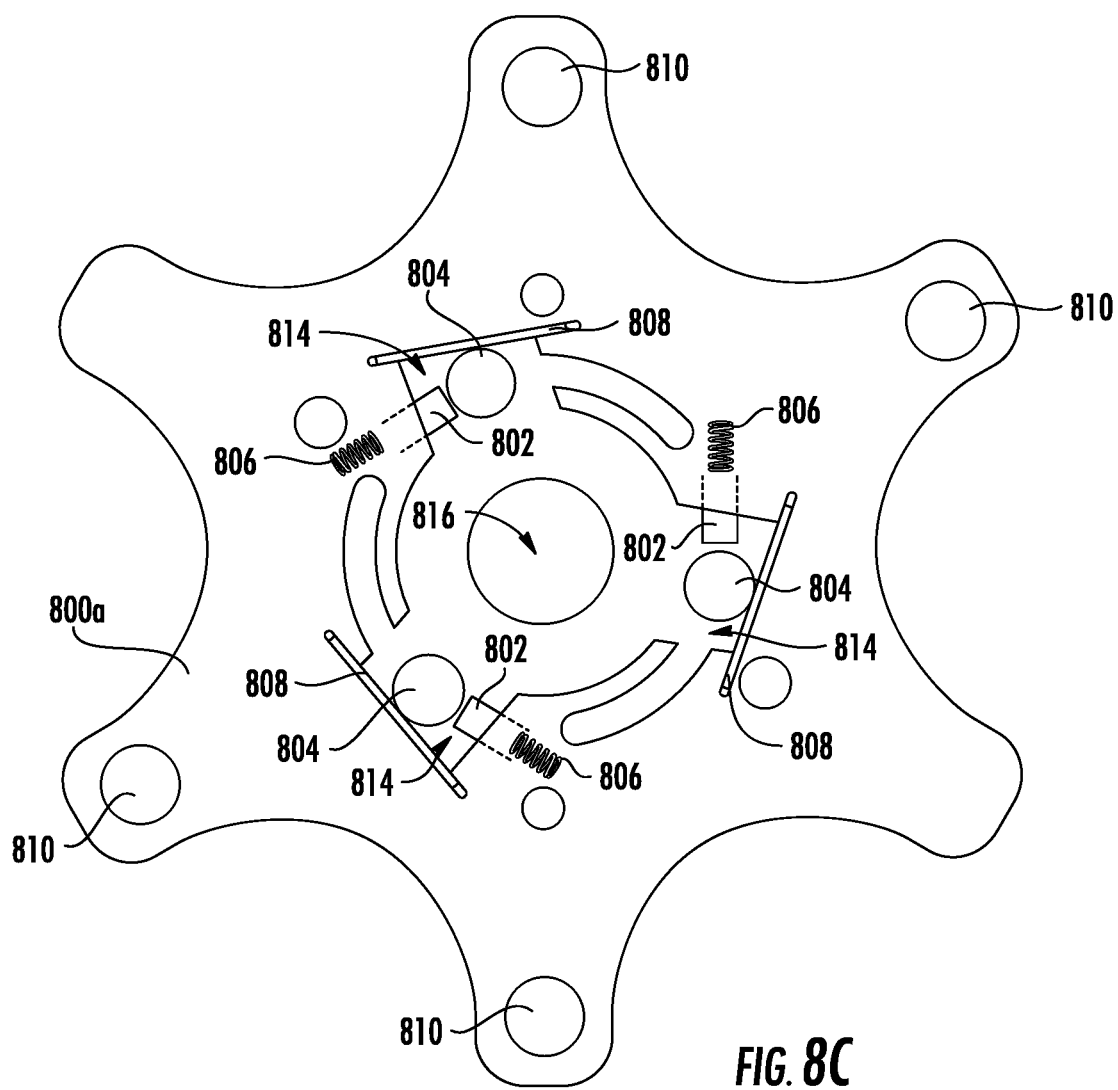
Figure 9C:
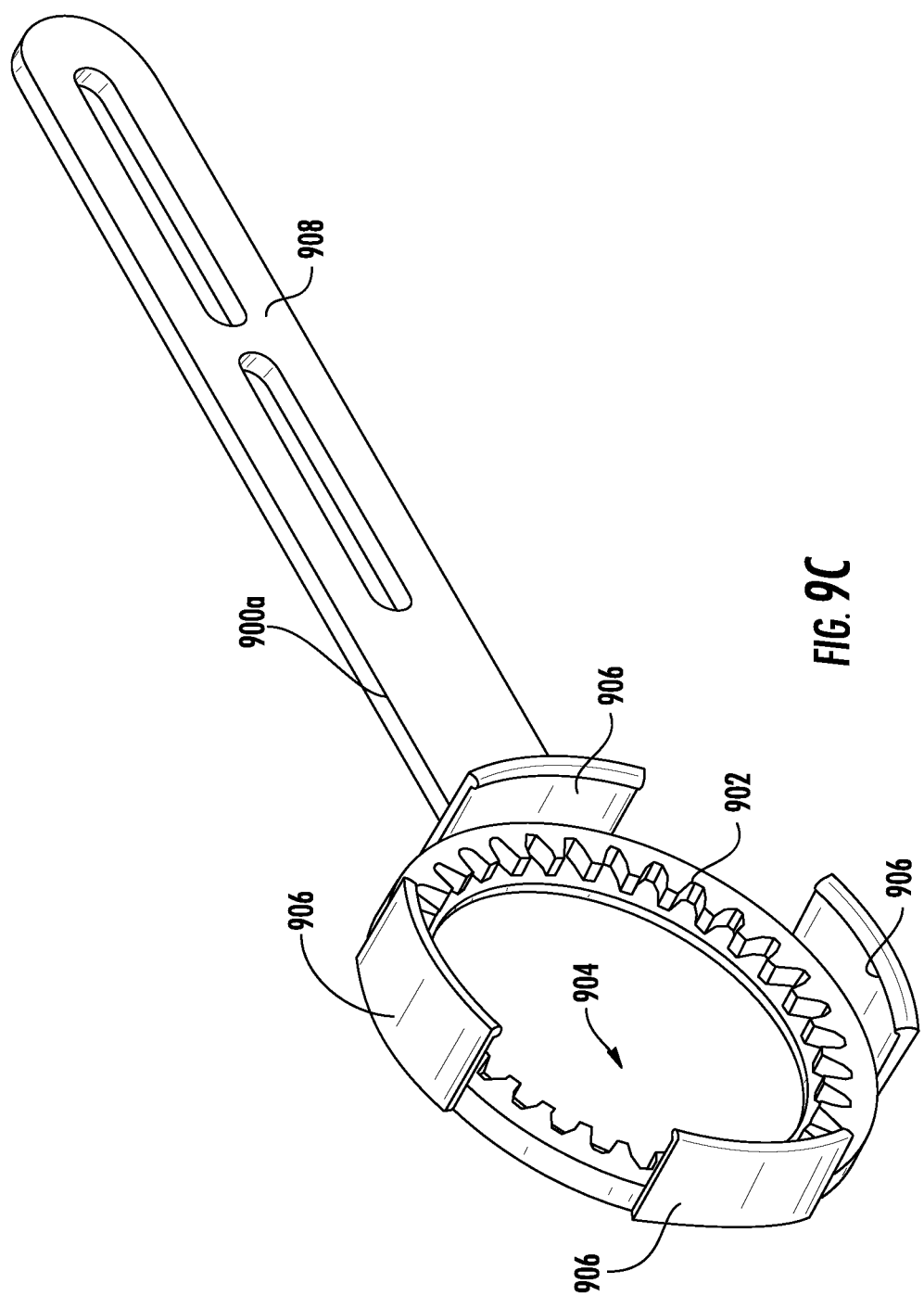
Figure 9D:
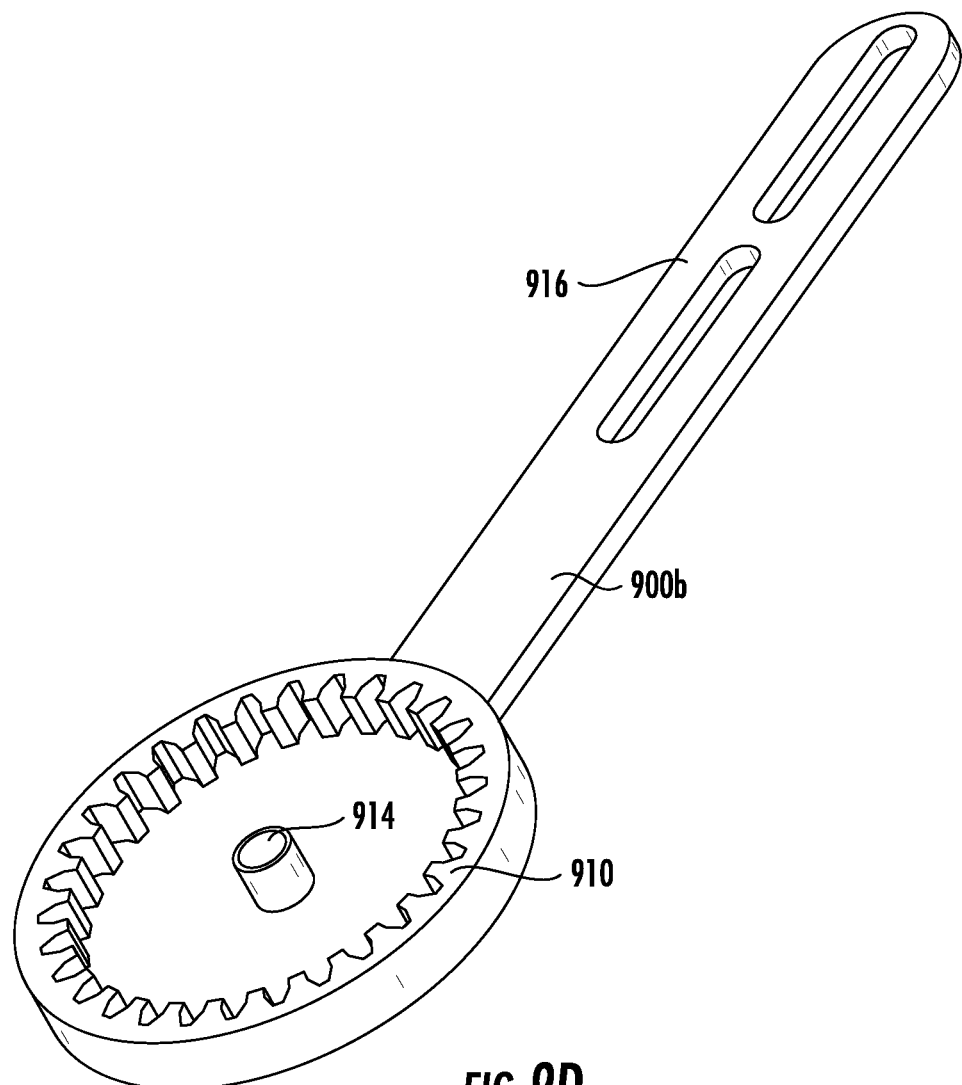
Figure 9E:
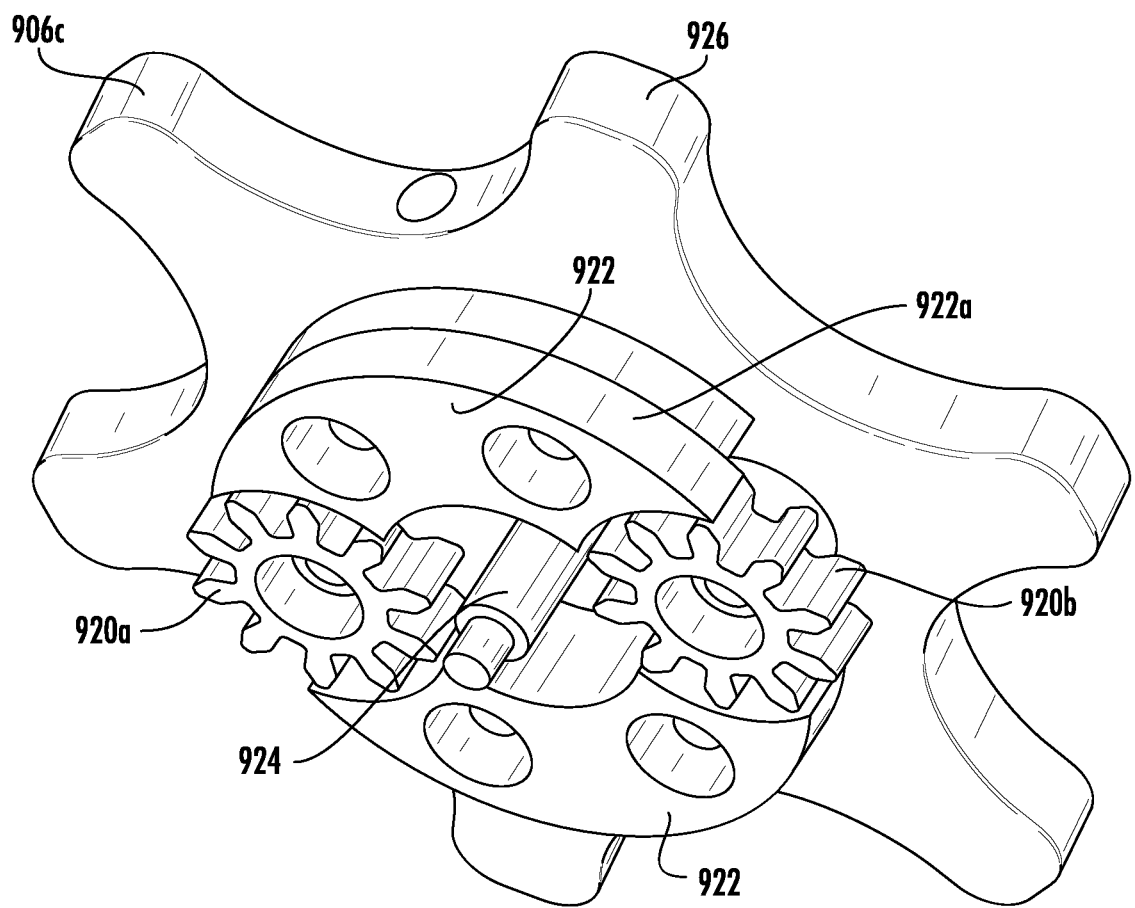
Figure 9F:
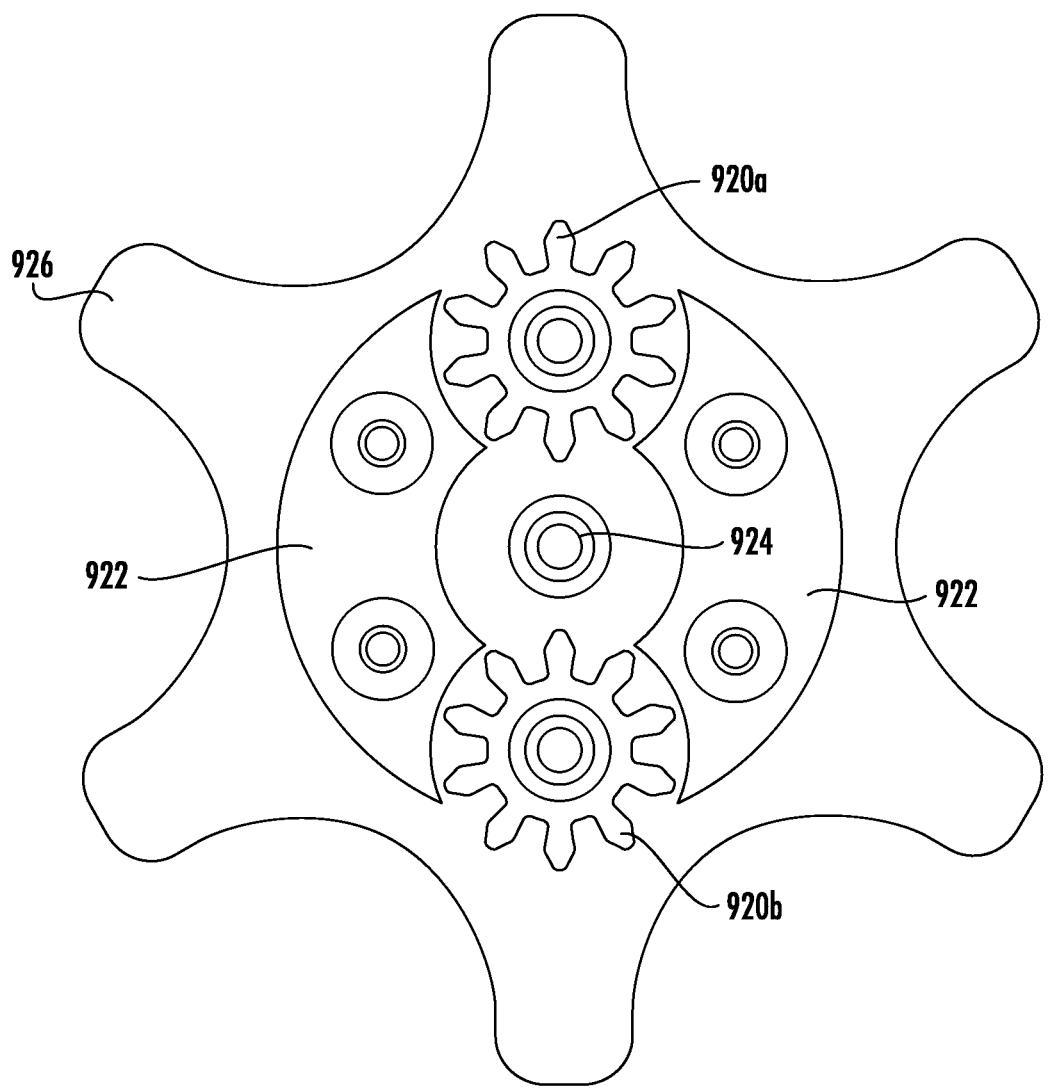
Figure 10A:
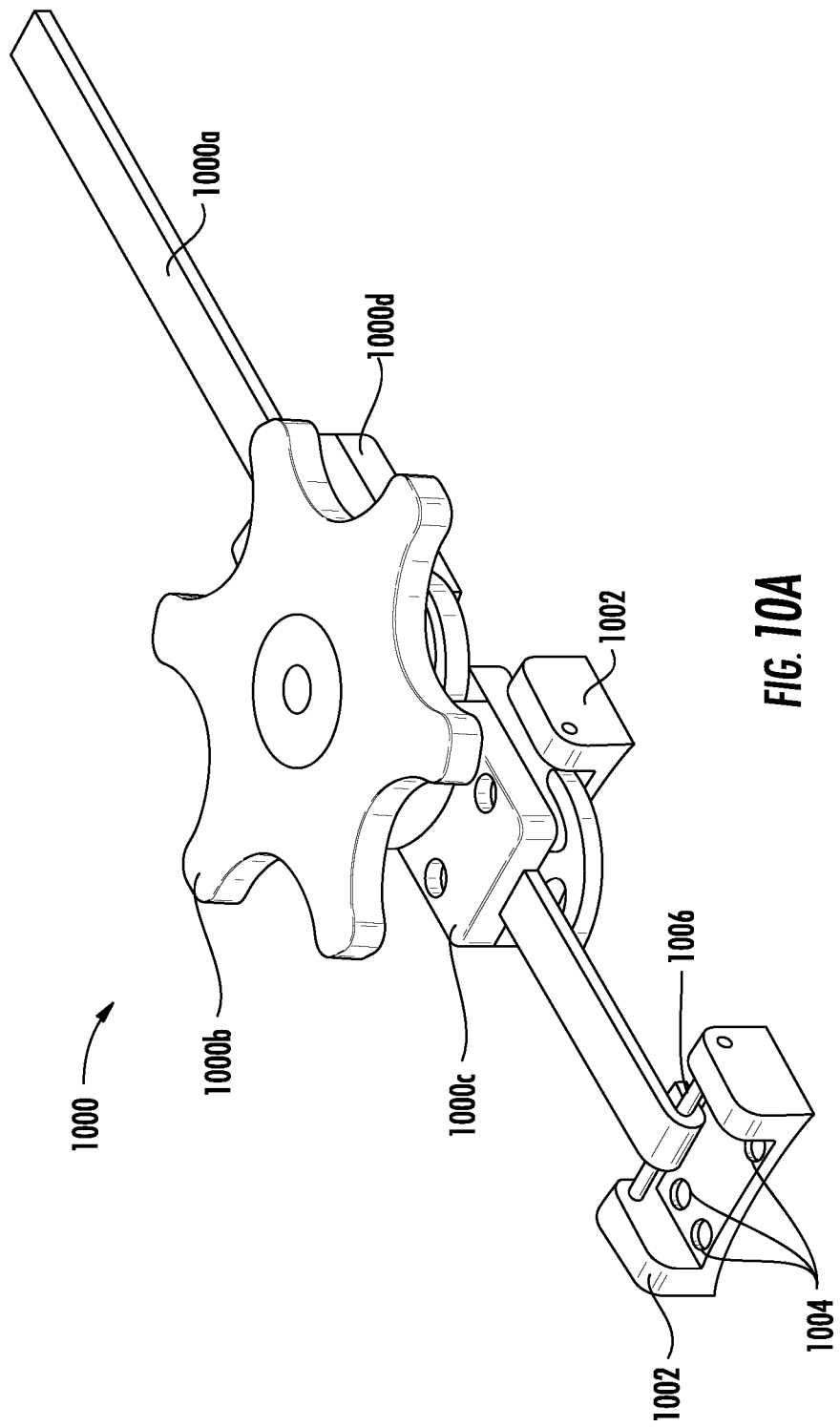
Figure 10E:
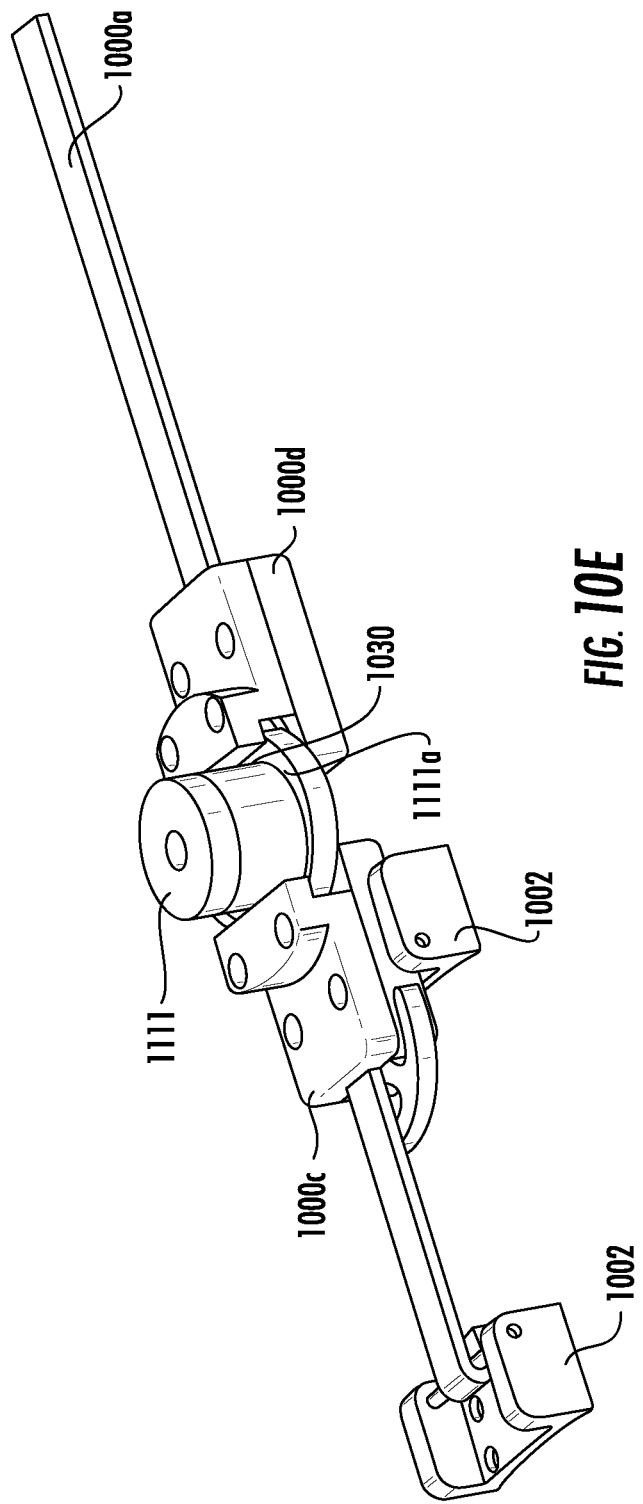
Figure 10G:
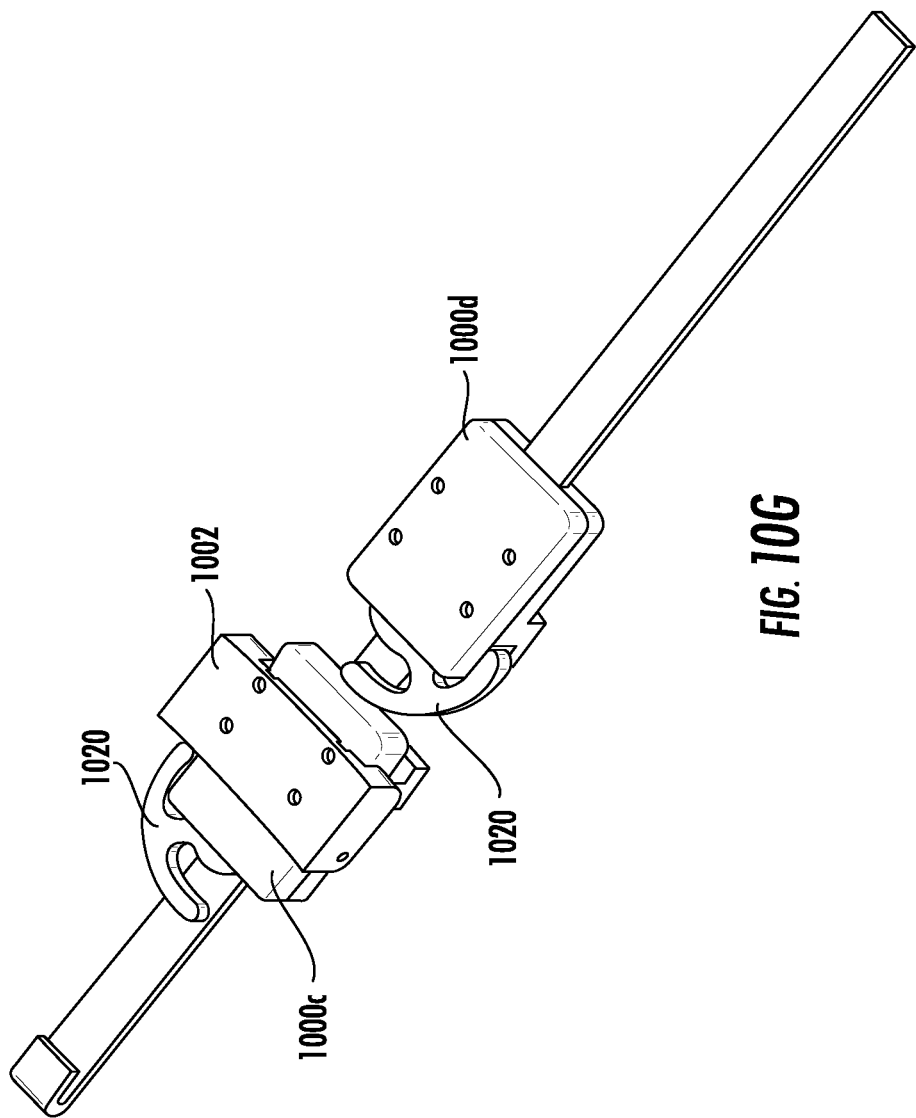
Figure 10H:
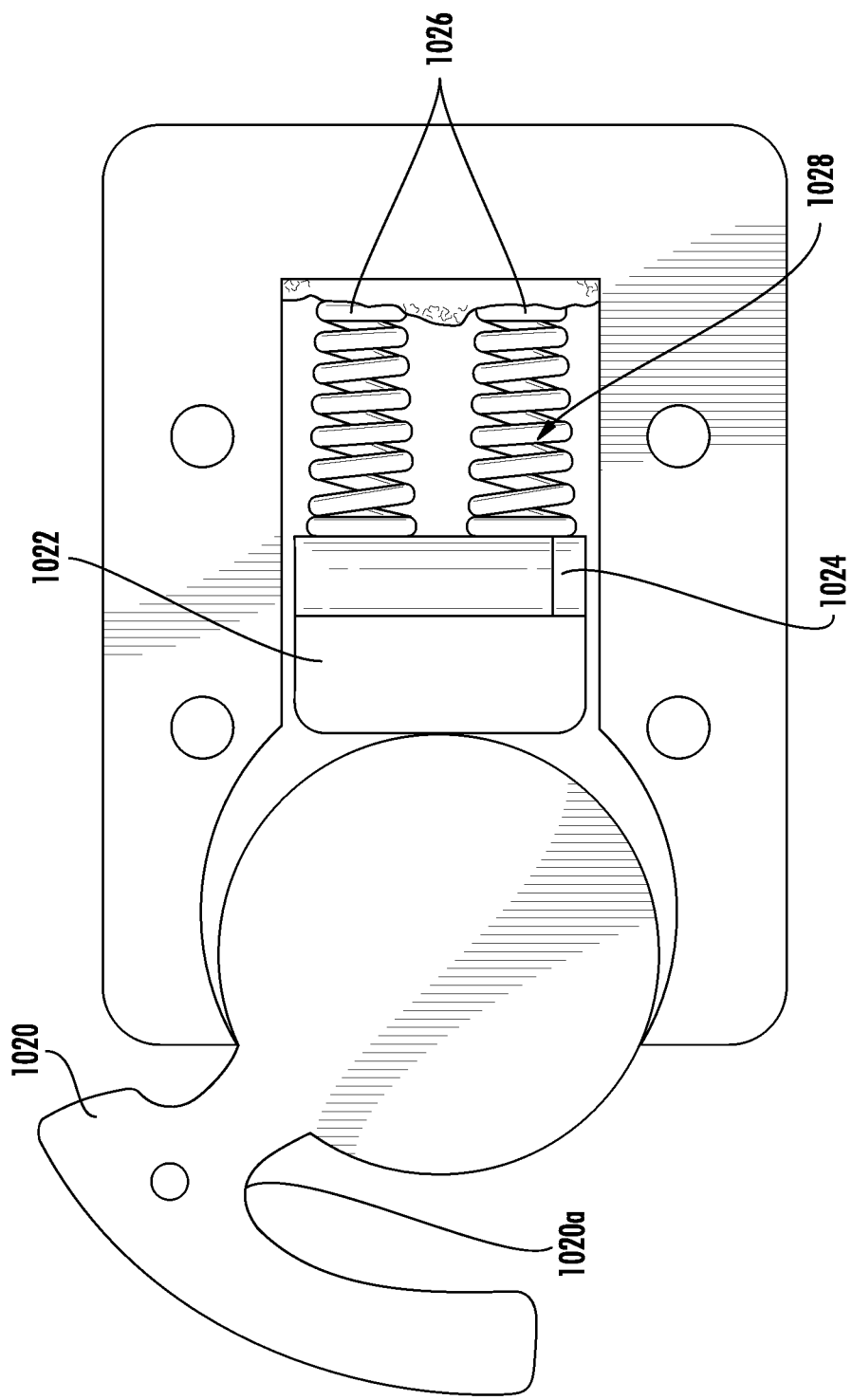

The rotational direction of the spool may be directed by the internal barrel 834 within the center of the dial mechanism, where the spool 812 may be configured to rotate in only one direction, or rotate in both directions, based on the configuration of the dial mechanism 800 with respect to the switch 800c. As illustrated in FIGS. 8B and 8C, when assembled one or more plungers 802, rollers 804, and springs 806 are positioned, within a plurality of recesses 814, in a circular orientation that corresponds to the one or more pins 830 within the switch 800c. The plunger 802 and the roller 804 may be defined by cylindrical components, and in one embodiment, the roller 804 may be positioned within the dial mechanism 800 in an upright orientation such that a top surface 804a of the roller 804 is flush with a top surface of the dial mechanism 800. In one embodiment, as shown in FIG. 8, the plunger 802 may be positioned within the dial mechanism 800 such that a top surface 802a of the plunger is adjacent to the side surface of the roller 804, and a bottom surface 802b of the plunger is operatively coupled with a spring 806 that is compressed within the interior of the dial mechanism 800. In such an embodiment, when the roller 804 is removed, the plunger 802 may be positioned within the dial mechanism 800 such that the plunger 804 fills the recess 814 and a tops surface 804a of the plunger 804 is adjacent to an interior side of the recess, and a bottom surface 802b of the plunger is operatively coupled with a spring 806 that is expanded within the recess 814 of the dial mechanism 800.

In one embodiment, the switch 800c may be mounted on the top of the upper dial member 800a, and positioned such that the side surface of the pins 830 are aligned with the side surface of the rollers 804, and in response to turning the switch 800c in a counter-clockwise direction the protrusions 832 are positioned within a first set of depressions 810a, and the pins 830 move in a lineal fashion towards the plungers 802. The coupling of the protrusions 832 within the depressions 810 may restrict free flowing movement and cause the switch 800c and the dial mechanism to be securely positioned with respect to one another. In another embodiment, the depressions may visually indicate the correct positioning for the switch. For example, the switch may be positioned in an "on" position in which the rollers 804 are engaged by the pins 830, or the switch may be positioned in an "off" position in which the rollers 804 are disengaged by the pins 830. In such an embodiment, in response to the counter-clockwise rotation of the switch 800c, the pins 830 may be configured to engage the rollers 804 such that the rollers 804 are caused to further compress the plungers 802 and springs 806 into the interior surface of the dial mechanism 800 allowing the roller 804 to be repositioned such that the dial can rotate in two directions. Specifically, the recess 814 may be defined by a channel having a width of "X" on a first end proximate to the plunger 802, and a narrower width of "Y" on a second end distal from the plunger 802 such that when the roller 804 is engaged by the pins 830 the roller 804 is repositioned proximate to the first end of the channel and the friction between the roller 804 and the barrel 834 is reduced or eliminated allowing the barrel 834 to freely rotate in a counter-clockwise and a clockwise direction resulting in the multidirectional rotation of the spool 812. As the barrel 834 rotates in the counter-clockwise direction the force applicator 319 may unwind from the spool 812 and further lengthen with respect to the dial mechanism. Alternatively, as the barrel 834 rotates in the clockwise direction the force applicator 319 may wind around the spool 812 and shorten with respect to the dial mechanism. It should be noted that, in such an embodiment, when the force applicator 319 is completely wound around the spool 812 the barrel 834 is restricted from further rotating in the clockwise direction.

In one embodiment, the switch 800c may be mounted on the top of the upper dial member 800a, and positioned such that the side surface of the pins 830 are aligned with the side surface of the rollers 804, and in response to turning the switch 800c in a clockwise direction the protrusions 832 are positioned within a second set of depressions 810b, and the pins 830 move in a lineal fashion away from the plungers 802. In such an embodiment, in response to the clockwise rotation of the switch 800c, the pins 830 may be configured to disengage the rollers 804 such that the rollers 804 and plungers 802 are expanded within the recess 814 of the dial mechanism 800 allowing the roller 804 to be repositioned such that the dial is restricted to rotate in one direction (e.g. clockwise). Specifically, the recess 814 may be defined by a channel having a width of "X" on a first end proximate to the plunger 802, and a narrower width of "Y" on a second end distal from the plunger 802 such that when the roller 804 is disengaged by the pins 830 the roller 804 is repositioned proximate to the second end of the channel and the friction between the roller 804 and the barrel 834 is increased restricting the barrel 834 from freely rotating in the counter-clockwise direction resulting in the one directional rotation of the spool 812 in the clockwise direction. The barrel 834 may be restricted from rotating in the counter-clockwise direction such that the force applicator 319 is restricted from unwinding from the spool 812 and further lengthening with respect to the dial mechanism. Alternatively, as the barrel 834 rotates in the clockwise direction the force applicator 319 may wind around the spool 812 and shorten with respect to the dial mechanism. It should be noted that, in such an embodiment, when the force applicator 319 is completely wound around the spool 812 the barrel 834 is restricted from further rotating in either the clockwise or counter-clockwise direction.

In one embodiment, as illustrated in FIGS. 9A through 9F, the force applicator mechanism 318 is embodied by a harmonic dial mechanism 900 having an upper dial member 900a, a lower dial member 900b, and a gear dial 900c where the upper dial member 900a and the lower dial member 900b pivot with respect to an axis, and the gear dial 900c is configured to control the rotational movement of the upper and lower dial members 900a, 900b when the gear dial 900c is actively engaging both the upper and lower dial members 900a, 900b. It should be noted that in such an embodiment at least a portion, and more specifically extended arms, of the upper dial member 900a and the lower dial member 900b may be defined by the upper and lower hinge plates 113, 114. In an exemplary embodiment, the harmonic dial mechanism 900 may be located at the elbow joint of the wearer, the lower hinge plate 114 may be defined by the extended arm of the upper dial member 900a, and the upper hinge plate 113 may be defined by the extended arm of the lower dial member 900b. The force applicator mechanism 318 may additional provide a pneumatic force in some embodiments.

The upper dial member 900a may comprise an upper set of teeth 902, an opening 904 for receiving and being operatively coupled with the gear dial 900c, a plurality of fasteners 906 configured for fastening the upper dial member 900a to the lower dial member 900c, and an extended arm 908. The lower dial member 900b may comprise a lower set of teeth 910, a bottom surface 912, a recess 914 configured for coupling with the gear dial 900c, and an extended arm 916. The gear dial 900c may comprise one or more planetary gears 920, at least one stopping mechanism 922, a rivet 924 configured for coupling with the lower dial member 900b, and a dial head 926, where the components of the gear dial 900c may be operatively coupled with the gear dial 900c via a plurality of apertures within the dial head 926 one or more attachments means including, but not limited to, nuts, bolts, screws, adhesive, other rivets, and the like. As such at least a portion of the recess 914 may be internally threaded, and at least a portion of the rivet 924 may be externally threaded such that the two components are configured to securely attach to one another. Additionally the harmonic dial mechanism 900 may be spring loaded such that a spring (not shown) is positioned around the rivet 924, where the spring is configured to aid in positioning the gear dial 900c with respect to the upper dial member 900a and the lower dial member 900b. Furthermore, the stopping mechanism 922 may comprise a ledge 922a that extends beyond the diameter of the opening 904 in the upper dial member 900a such that when the top surface of the ledge 922a reaches the opening 904, the ledge 922a stops the motion of the gear dial 900c, and the gear dial 900c is restricted from being positioned beyond the opening 904 of the upper dial member 900a. In this way the gear dial 900c is configured to be contained within a housing defined by the upper and lower dial members 900a, 900b.

In one embodiment, the gear dial 900c is positioned in a first position such that the planetary gears 920 engage both the upper and lower set of teeth 902, 910. In such an embodiment the top surface of the planetary gears 920 may be positioned proximate to the opening 904 of the upper dial member 900a such that there is a recess between the upper dial member 900a and the dial head 926. In one embodiment, the first set of teeth 902 may comprise more teeth than the second set of teeth 910, or vice versa, such that the gear ratio between the planetary gears 920 and the first set of teeth 902 is different than that gear ratio between the planetary gears 920 and the second set of teeth 910. In this way, when the dial head 926 is turned the extended arms of the upper and lower dial member 908, 916 move, rotate, and/or pivot with respect to one another. In an alternate embodiment, the first planetary gear 920a may comprise more teeth than the second planetary gear 920b, or vice versa, such that the gear ratio between the first planetary gears 920s and the first and second set of teeth 902, 910 is different than that gear ratio between the second planetary gears 920b and the first and second set of teeth 902, 910. In this way, when the dial head 926 is turned the extended arms of the upper and lower dial member 908, 916 may incrementally move, rotate, and/or pivot with respect to one another such that the gear dial 900c maintains the position of the first and second set of teeth 902, 910 and does not allow for free movement of the extended arms 908, 916 or back drive of the current position. The gear dial 900c may be rotated either clockwise or counter-clockwise such that the harmonic dial mechanism 900 may promote either the extension of flexion of the elbow joint of the wearer.

In another embodiment, the gear dial 900c is positioned in a second position such that the planetary gears 920 is disengaged from the upper set of teeth 902, and engages the lower set of teeth 910. In this way the gear dial 900c may be configured to freely rotate either clockwise or counter-clockwise based on the natural motion of the wearer, where the current position may be locked into place my moving the gear dial 900c back into the first position. In such an embodiment the bottom surface of the planetary gears 920 may be positioned proximate to the bottom surface 912 of the lower dial member 900b such that the top surface of the planetary gears 920 is flush with the top surface of the second set of teeth 910, and the bottom surface of the dial head 926 is adjacent to the top surface of the upper dial member such that there is not a recess between the upper dial member 900a and the dial head 926. In this way, when the dial head 926 is turned the extended arms of the upper and lower dial member 908, 916 move, rotate, and/or pivot with respect to one another. In such an embodiment, the extended arms of the upper and lower dial member 908, 916 may continuously move, rotate, and/or pivot with respect to one another.

In one embodiment, as illustrated in FIGS. 10A through 10H, the force applicator mechanism 318 is embodied by a dual friction lock mechanism 1000 having a friction lock bar 1000a, a rotary dial 1000b, and a first and a second friction lock member 1000c, 1000d, respectively, where the first and second friction lock members 1000c, 1000d are configured to either incrementally move linearly along the friction lock bar 1000a in an "inchworm" like motion with respect to one another, or continuously move linearly along the friction lock bar 1000a. The dual friction lock mechanism 1000 may further comprise and/or be coupled with one or more hinge plates via an attachment member 1002. The attachment members 1002 may be defined by a component having a plurality of apertures 1004 for receiving rivets and a rod 1006 configured to operatively couple with at least a portion of the friction lock bar 1000a. Furthermore, the bottom surface of the attachment members 1002 may be shaped such that they correspond to the attaching member. For example, the attachment members 1002 may be curved (as illustrated) if being attached to a curved bar or hinge plate, or the attachment members 1002 may be straight if being attached to a straight bar or hinge plate.

The rotary dial 1000b may comprise a dial head 1110, a camshaft 1111, and a base and/or bottom surface 1112 configured to be coupled with the friction lock bar 1000a. In this way, at least a portion of the bottom surface 1112 of the rotary dial 1000b may be sized and shaped such that it can be securely attached to the friction lock bar 1000a. When the friction lock bar 1000a is positioned within the bottom surface 1112 of the rotary dial 1000b, the friction lock bar 1000a is flush with the bottom surface 1112 of the rotary dial 1000b. The camshaft 1111 of the rotary dial 1000b may be substantially oval shaped and may comprise a recess 1111a configured for receiving and/or be operatively coupled with at least a portion of the first and second friction lock members 1000c, 1000d.

The first and second friction lock members 1000c, 1000d may each comprise a switch 1020, a plate 1022, a roller 1024, and springs 1026, where the orientation of the switch 1020 repositions the roller 1024 such that the movement of the roller 1024 is either restricted to one direction, or enabled for movement in two directions (e.g. forwards and backward). An optional piece of material (e.g. foam) may be placed between the springs 1026. It should be noted, that although the illustrated embodiments depict a plastic plate 1022, the plate 1022 may be formed of any suitable material not explicitly contemplated or illustrated herein (e.g. metal). Furthermore, in some embodiments, the plate 1022 may be optionally removed and the switch 1020 may directly engage the roller 1024.

The switch 1020 may be configured to lock the position of the first and second friction lock members 1000c, 1000d with respect to the friction lock bar 1000a such that the first and second friction lock members 1000c, 1000d are configured to only incrementally move linearly in one direction and do not back drive and/or move in the opposite direction. In such an embodiment, the switch 1020 may be centrally positioned such that the neck 1020a of the switch is perpendicular to the roller 1024, and the switch 1020 either directly or indirectly (e.g. via the plate 1022, engages the roller 1024 such that the roller 1024 is positioned proximate to a narrow and/or tapered end 1028a of a recess 1028, in which the roller 1024 and springs 1026 are positioned, within the first and second friction lock members 1000c, 1000d. In this way, the movement of the roller 1024 is restricted by the friction between the roller 1024 and the tapered end 1028a.

Alternatively, the switch 1020 may be configured to release and/or allow for a release of the position of the first and second friction lock members 1000c, 1000d with respect to the friction lock bar 1000a such that the first and second friction lock members 1000c, 1000d are configured to continuously move linearly in two directions (e.g. forwards/backwards, up/down) with respect to the friction lock bar 1000a. In such an embodiment, the switch may be offset proximate to an edge of the first and second friction lock members 1000c, and positioned such that the neck 1020a of the switch is acutely angled with respect to the roller 1024, and the roller 1024 is positioned proximate to a wider end 1028b of a recess 1028, in which the roller 1024 and springs 1026 are positioned, within the first and second friction lock members 1000c, 1000d. In this way, the roller 1024 is disengaged from the tapered end 1028a, and the movement of the roller 1024 is not restricted by the friction between the roller 1024 and the narrower tapered end 1028a.

A ledge 1030 of the first and second friction lock members 1000c, 1000d may be configured for being operatively coupled with the a recess 1111a in the camshaft 1111 of the rotary dial 1000b. As such the ledge 1030 may extend into the recess 1111a such that the first and second friction lock members 1000c, 1000d are coupled with one another via the camshaft 1111, and the first and second friction lock members 1000c, 1000d may move in relation to one another based on the orientation of the camshaft.

In one embodiment, the switch 1020 may be centrally positioned such that the neck 1020a of the switch is perpendicular to the roller 1024, the roller 1024 is positioned with the tapered end 1028a of the recess 1028 to restrict the movement of the first and second friction lock members 1000c, 1000d to one linear direction along the friction lock bar 1000a. Specifically, in response to turning the friction lock dial 1000b in either a clockwise or counter-clockwise motion, the camshaft 1111 moves the first and second friction lock members 1000c, 1000d apart from one another as its longer axis aligns with the first and second friction lock members 1000c, 1000d. In such an embodiment, only the first friction lock member 1000c is incrementally advanced forward along the friction lock bar, and the second friction lock member 1000d remains in a static position as the first friction lock member 1000c moves forward. As the friction lock dial 1000b is further rotated, the camshaft moves the first and second friction lock members 1000c, 1000d back towards one another as its shorter axis aligns with the first and second friction lock members 1000c, 1000d. In such an embodiment, only the second friction lock member 1000d is incrementally advanced forward along the friction lock bar, and the first friction lock member 1000c remains in a static position as the second friction lock member 1000d moves forward. In this way, the first and second friction lock members 1000c, 1000d alternate motion as they "inch" or incrementally advance along the friction lock bar 1000b similar to the motion of an inchworm.

In another embodiment, the switch may be offset proximate to an edge of the first and second friction lock members 1000c such that the neck 1020a of the switch is acutely angled with respect to the roller 1024, and the roller 1024 is positioned proximate to a wider end 1028b of a recess 1028 to enable the continuous movement of the first and second friction lock members 1000c in two linear directions along the friction lock bar 1000a. Specifically, in response to sliding the first and second friction lock members 1000c, 1000d forwards and/or backwards with respect to the friction lock bar 1000b the first and second friction lock members 1000c, 1000d may be continuously repositioned with respect to the friction lock bar 1000b. In this way, the first and second friction lock members 1000c, 1000d may be configured to embody a free flowing movement as they are slid back and forth on the friction lock bar 1000a.

Figure 11A:
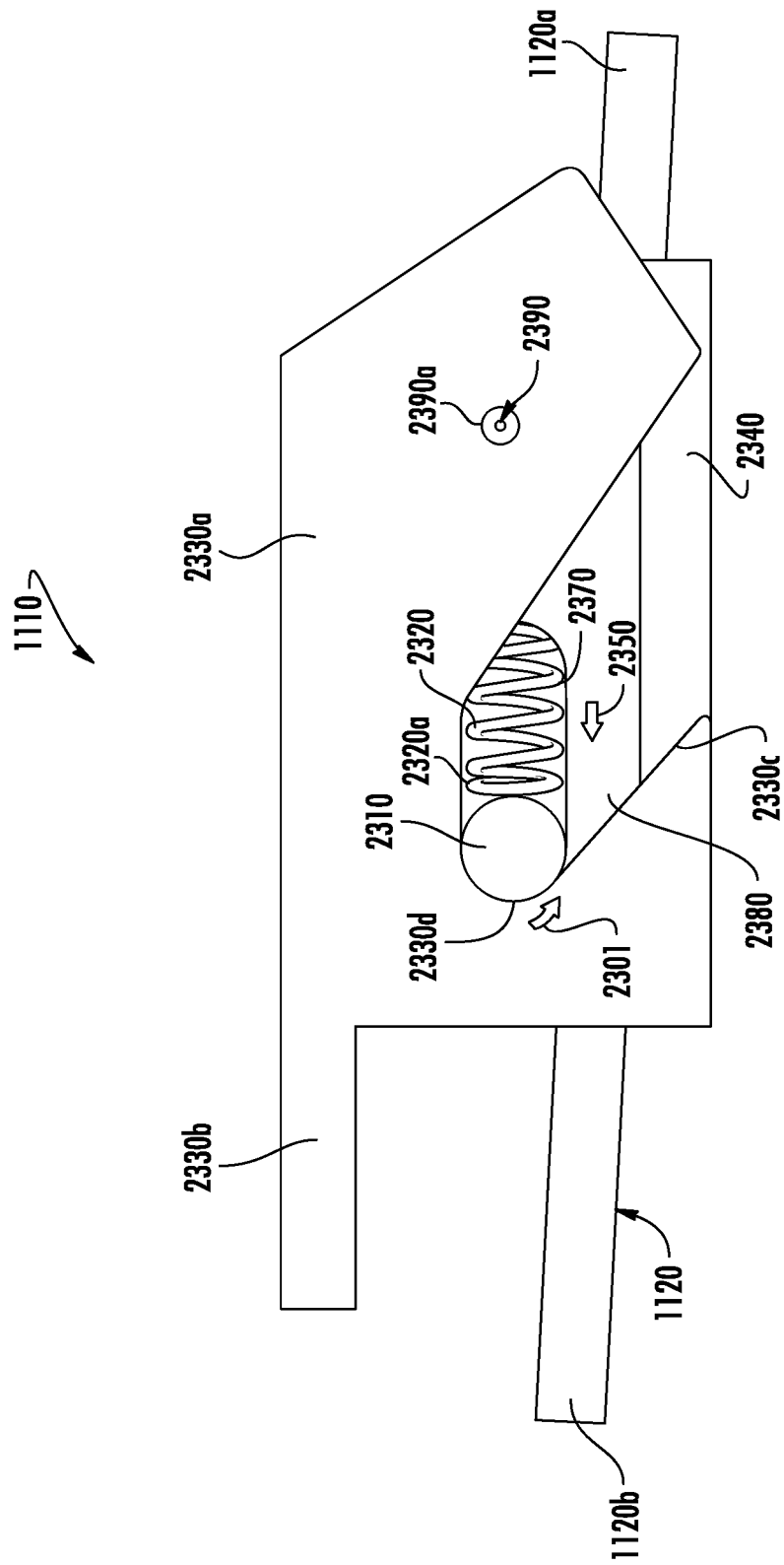

FIGS. 11A-E illustrate an embodiment of a friction lock 1110 device, as may be used throughout this disclosure and with various embodiments of the invention. Referring to FIG. 11A, the friction lock 1110 comprises a base 2340, a main body 2380, a latch 2330, a roller 2310, a spring 2320, a recess 2370, and a pivot pin 2390a. The friction lock 1110 may engage a sliding bar 1120, as described in several embodiments herein. Each of these elements may be comprised of a metal, solid plastic, wood, or other substantially rigid material. The spring may be any type of coiled spring that may compress and expand. The sliding bar enters an alley 2370a that is approximately the width and height of the sliding bar 1120. The alley 2370a may be formed between the base 2340 and the main body 2380. The base 2340 and the main body 2380 may be connected by bolts, screws, nails, glue, adhesive, or in any other manner that secures the two parts together. In another embodiment, the base 2340 and the main body 2380 may be one solid piece and therefore the alley 2370a may pass through the combined base/main body member of the friction lock 1120. In one embodiment, the base 2340 of the friction lock 1110 is attached to a rigid surface such that the friction lock 1110 is securely fastened to the surface. In another embodiment, the base 2340 of the friction lock 1120 is slidably fastened to a surface such that the friction lock may slide along the surface without being separated from the surface. In one embodiment, the base 2340 of the friction lock 1110 is pivotally connected to a surface such that the entire friction lock 1110 may pivot about an axis perpendicular to the surface without separating from the surface.

The main body 2380 comprises a recess 2370, which houses a spring 2320 and a roller 2310. The roller 2310 is always in contact with the sliding bar 1120 which is positioned underneath the roller 2310. The spring 2320 comprises a first end 2320a that engages the roller 2310, and a second end 2320b that engages main body 2380 at a wall 2380a. The engagement of the main body 2380 and the second end of the spring 2320b at the wall 2380a is illustrated in the cross-section depiction of the friction lock shown in FIG. 11C. The spring provides a force 2350 on the roller 2310, causing the roller 2310 to roll away from the wall 2380a. The pivot pin 2390a runs through the main body 2380 and defines a pivot axis 2390. The latch 2330 is operatively coupled to the main body 2380 via the pivot pin 2390a such that the latch 2330 may rotate about the pivot axis 2390. The latch comprises a body 2330a, a lever 2330b, an unlocking interface 2330c, and a locking interface 2330d. The unlocking interface 2330c and the locking interface 2330d are illustrated with bolded lines, and generally comprise the surface area at the bolded areas.

Figure 11B:
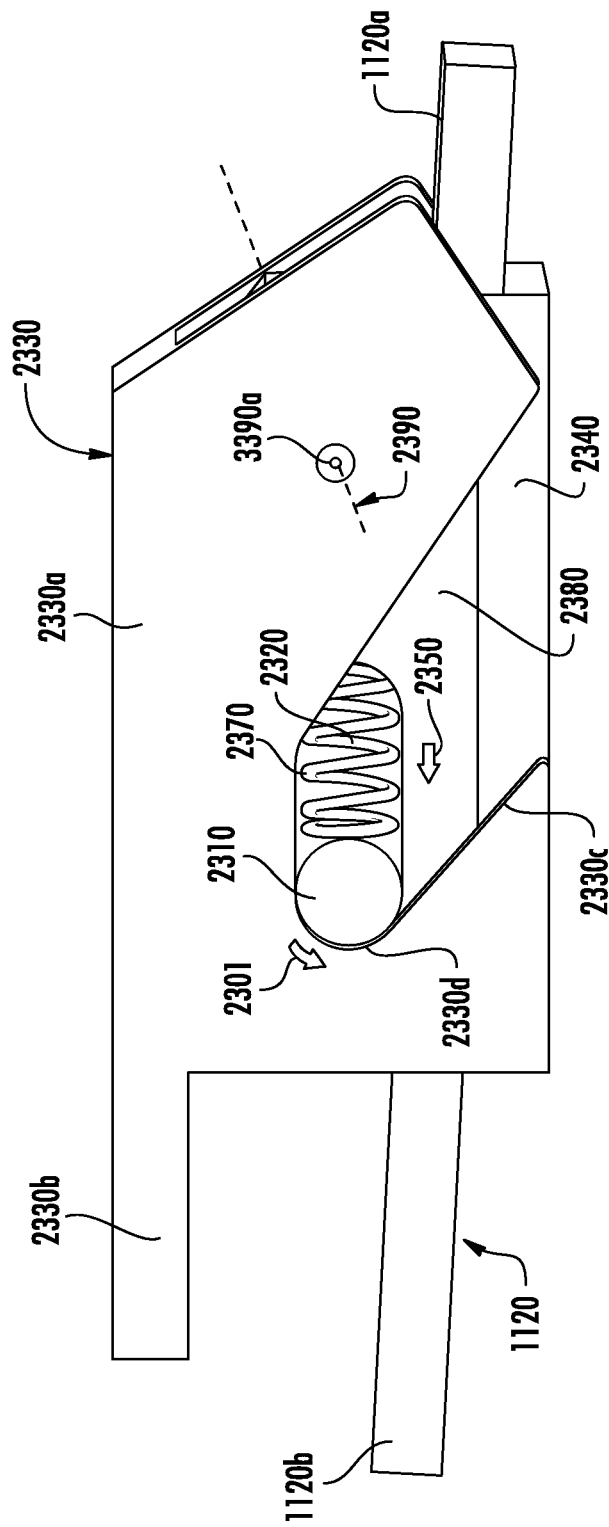
Figure 11C:
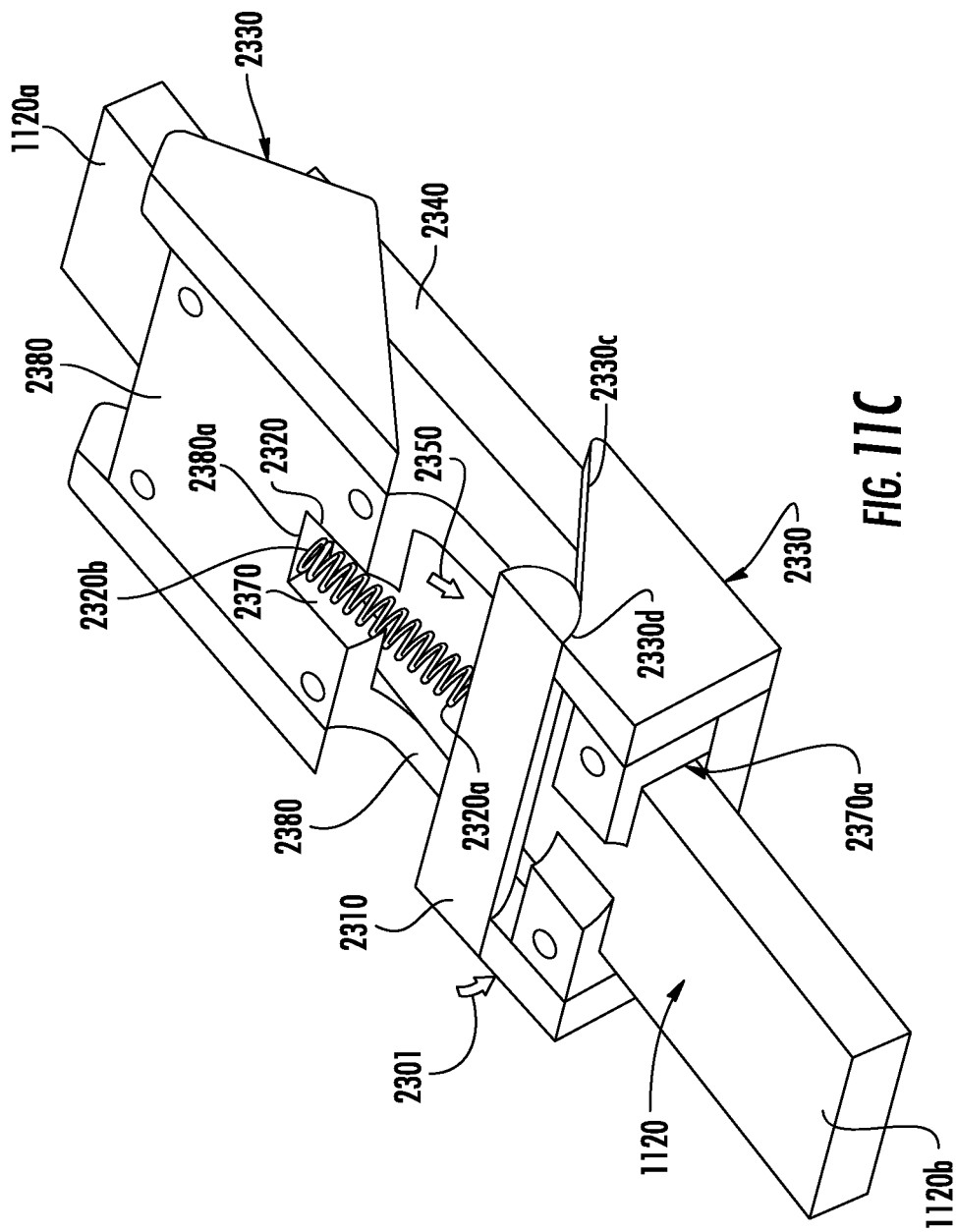
Figure 11E:
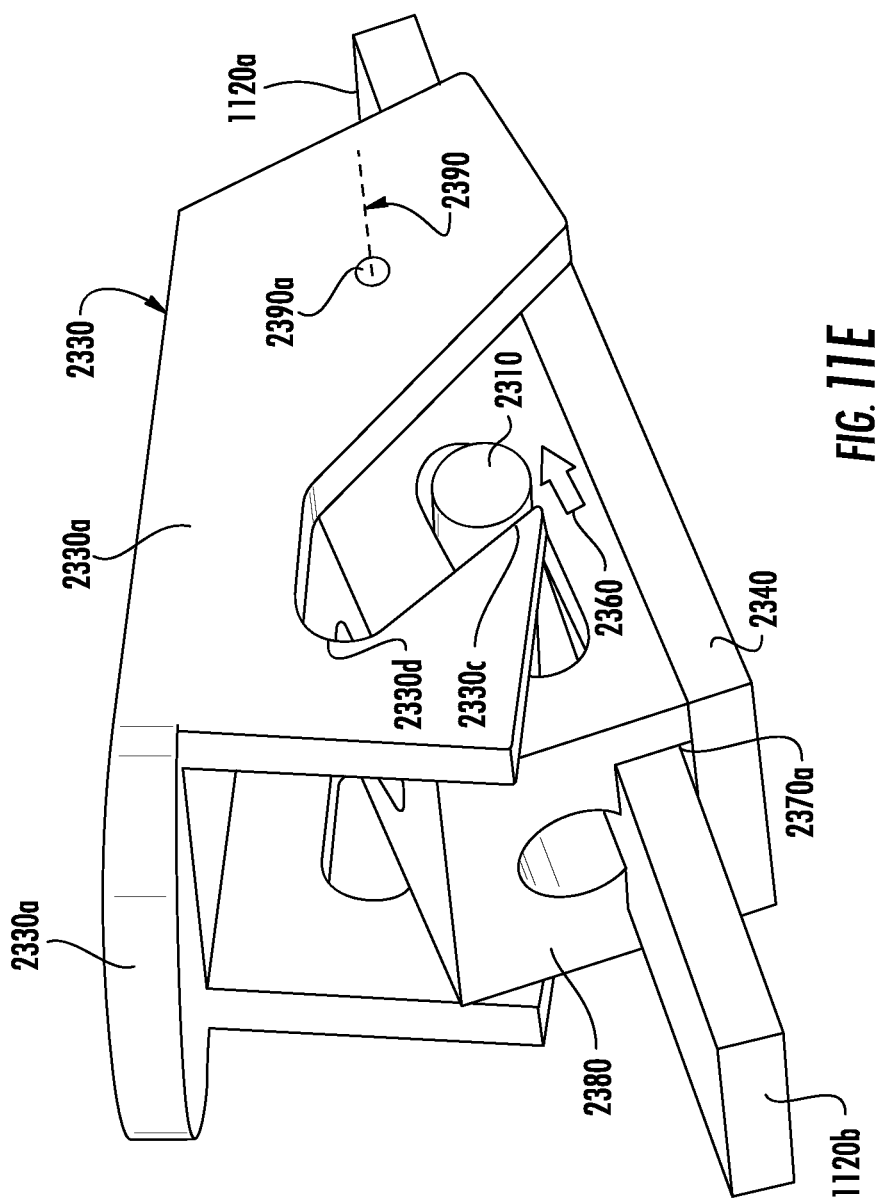

The friction lock 1110 has two modes: a locked mode, illustrated in FIGS. 11A-C, and an unlocked mode, illustrated in FIGS. 11D-E. In the locked mode, the latch 2330 is positioned such that the spring 2320 can extend the roller 2310 across the recess 2370 such that the roller 2310 is in contact with the latch at the locking interface 2330d. In such a position, the spring 2320 is applying a force 2350 on the roller 2310 such that the roller 2310 is pressed up against the locking interface 2330d. The locking interface 2330d is tapered such that the locking interface surface 2330d has approximately the same arc as the roller 2310 at the position where the roller 2310 engages the locking interface 2330d, and the locking interface 2330d has a wider arc in the positions not engaging the roller 2310, when the friction lock is in the locked position. The force 2350 applied by the spring 2320 increases the static friction between the roller 2310 and the locking interface 2330d. Therefore, when a force is applied to the sliding bar 1120, in the direction of a second end 1120b from a first end 1120a, the sliding bar 1120 engages the bottom of the roller 2310 and a clockwise force is applied to the roller 2310. However, the high static force 2301 of the roller 2310 and locking interface 2330d engagement creates a counter-force equal to clockwise force created by the sliding bar 1120. The roller 2310 therefore is pinched between the locking interface 2330d and the sliding bar 1120 such that neither the roller 2310 nor the sliding bar 1120 may roll or slide, respectively. Therefore, the friction lock 1110 is a restriction mechanism for a sliding bar 1120 traveling in a direction from a first end 1120a towards a second end 1120b.

Continuing with the locked mode of the friction lock 1110, if the sliding bar 1120 travels in a second direction, travelling from the second point 1120b toward the first point 1120a, the friction lock 1120 does not restrict the sliding movement. In such an embodiment, the sliding bar 1120 engages the bottom of the roller 2310 and creates a counter-clockwise force on the roller, along with a general force in the direction of the travelling path of the sliding bar. The force applied to the roller 2310 cause the roller 2310 to rotate in a direction away from the locking interface 2330d. As the surface of the latch 2330 is wider at the areas beyond the locking interface 2330d, the roller is not pinched into a surface of the latch 2330 and therefore only the static and sliding friction forces of the interface of the roller 2310 and the spring 2320 are resistive to the turning force of the roller 2310. In one embodiment, these friction forces are small enough, relative to the force applied by the sliding bar 1120, that the roller 2310 is able to roll. As the roller 2310 rolls in the counter-clockwise manner, the sliding bar 1120 may slide underneath the roller 2310 in the direction of the force applied to the sliding bar 1120. Therefore, even when the friction lock 1120 is in a "locked" position, the friction lock 1120 still allows a sliding bar 1120 to travel in one direction, while completely restricting movement of the sliding bar 1120 in the opposite direction.

The second mode of the friction lock 1120 is the unlocked mode, illustrated in FIGS. 11D-E. In this embodiment, the latch 2330 is in a second position defined by a rotation about the pivot axis 2390 such that the unlocking interface 2330c of the latch 2330 engages the roller 2310. As illustrated in FIGS. 11D-E, moving the latch 2330 into this second position causes the latch 2330 to roll the roller 2310 into the spring 2320, compressing the spring 2330 such that the roller 2310 is closer to the wall 2380(a) (illustrated in FIG. 11C) when the latch 2330 is in this second, unlocked, position than when the latch is in the first, locked, position.

As the latch is a flat, ramped surface, relative to the roller, the spring's 2320 force 2350 on the roller 2310 generally causes the roller 2310 to upward, away from the sliding bar 1120. In some embodiments, the roller 2310 is completely separated from the sliding bar 1120. In other embodiments, the roller 2310 still engages the sliding bar 1120, but no significant friction force is applied to the roller 2310 that could prevent the roller 2310 from rolling. As such, the sliding bar 1120 may slide beneath the sliding bar (either engaging and rolling the roller 2310, or not engaging the roller 2310) relatively freely without restriction of movement in either direction.

While some embodiments of the device disclosed herein comprise a first arm member, a second arm member, and a hinge or pivot, some embodiments do not comprise a pivoting connection between the first and second arm members. In one embodiment, no hinge is provided between the first and second arm members such that the elbow of the user 314 is the only hinged aspect of the device. In some embodiments, a living hinge may be provided, where the living hinge is a rubber or elastic connector between the two arm members that is very flexible in every direction, exerting very little force on the user such that the user's elbow comprises the main rotational element of the assembly. In one embodiment, the two arm members are connected by more than one pivoting hinge. In such an embodiment, the two or more hinges may pivot about the same axis, pivot along parallel axes to each other, or pivot along non-parallel axes. In one embodiment comprising multiple hinges, the multidirectional configuration of the hinges may allow for a full range of motion about the elbow, and not the unidirectional range of motion allowed by a single hinge.

According to various embodiments of the invention, one or more devices, systems, components, apparatuses may perform one or more process or method steps. As generally discussed in this description, for example, a device component may apply a force, direct a force, receive a force, engage a body part, manipulate a body part, engage and/or be operatively coupled to one or more other components, and/or function, perform, take action and/or any other method or process step described herein. Accordingly, embodiments of the invention include various methods for assisting with pronation and/or supination and/or extension and/or flexion of one or more body parts of a user as implemented in whole or in part by device components described herein, and in some cases, components not described herein and/or manual method or process steps.

According to various embodiments of the invention, assistance may be provided to (or about) any body part and/or joint of a user's body. While various embodiments described herein may specifically refer to a device that is used to provide assistance, for example, to an elbow joint of the user, to a wrist joint of the user, or to provide pronation and/or supination assistance, it should be understood that the devices, systems, components, apparatuses and the like discussed in this description may be used to assist other joints, including, but not limited to shoulders, hips, knees, ankles, knuckles, finger joints, toe joints and/or the like.

Referring now to FIG. 12, a flowchart illustrates a method 1200 for manipulating a hand of a user to provide pronation and/or supination assistance according to embodiments of the invention. The first step, as represented by block 1210, is to engage the hand of the user using a hand engagement member. The next step, represented by block 1220, is to apply a force to the hand engagement member to urge the hand engagement member to rotate about a longitudinal axis of an arm of the user using a force application mechanism. This provides pronation or supination assistance to the user. In some embodiments, the hand engagement member is operatively coupled to an anchor.

Engaging the hand of the user (step 1210) may include engaging the hand without engaging a wrist or forearm of the user. In other words, the hand engagement member engages only the hand of the user and does not engage the wrist or the forearm in some embodiments. In some embodiments, engaging (step 1210) may include continuously engaging the hand of the user while the force is applied.

In some embodiments, the method also includes, as represented by block 1230, operatively coupling the hand engagement member to an anchor using an attachment member. In some such cases, operatively coupling includes tethering. In some cases, on the other hand, the hand engagement member is not operatively coupled to the anchor, but is partially or completely free from the anchor.

In some embodiments, the method also includes, as represented by block 1240, applying an attachment force to urge the hand engagement member into a non-engaged position when the hand engagement member is disengaged from the hand of the user.

In some embodiments, the hand engagement member is configured to move from a first engaged position to a second engaged position when the force is applied by the force application mechanism. In some such embodiments, when the hand engagement member is moved from the first engaged position to the second engaged position, the hand engagement member causes the hand to rotate or move in an arcuate range of motion substantially about a longitudinal axis of an arm of the user. Furthermore, in some such embodiments, when the hand engagement member is moved from the first engaged position to the second engaged position, the hand engagement member allows the hand to move in a natural range of motion as the arm is pronated or supinated.

As used herein, the term "operatively coupled" is intended to refer to two or more devices, systems, components, apparatuses, body parts and/or the like being rigidly attached or connected, non-rigidly attached or connected, in mechanical communication with one another, directly attached or connected, indirectly attached or connected (for example, with one or more intermediate devices, systems, components, apparatuses, body parts and/or the like being interposed, disposed, attached, connected, coupled or the like in between). In various instances, operatively coupled refers to permanent, semi-permanent, detachable, removable, separable, inseparable, or other types of couplings.

As used herein, the term "proximate" is intended to refer to a relationship wherein two or more devices, systems, components, apparatuses, body parts and/or the like are disposed, interposed, placed, situated, connected, attached, coupled, operably coupled in a relatively close relationship. Proximate may refer to physical contact, substantially physical contact, or nearby. "Proximate an edge" is intended to refer to adjacent an edge, substantially adjacent an edge, near an edge, on an edge or the like. "Proximate a portion" is intended to refer to adjacent a portion, substantially adjacent a portion, near a portion, on a portion or the like.

In various embodiments described herein, a force applicator may be or include a cable, belt, line, elastic band, inelastic band, chain, wire, ribbon, some combination of the foregoing, and/or the like. In various embodiments, a force application mechanism may refer to any mechanism that applies a force, such as, but not limited to any of the force application mechanisms described herein, harmonic drive mechanisms, pneumatic drive mechanisms, planetary gear mechanisms, rotary mechanisms (e.g., continuous, non-incremental, incremental and/or the like), inflatable members, manual (e.g., user-generated) force application, winches, springs, and/or the like.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. A device for manipulating a hand of a user to provide pronation or supination assistance, the device comprising:
   an anchor;
   a hand engagement member operatively coupled to the anchor and configured to receive and engage the hand of the user;
   a non-rigid force applicator comprising a member portion and an anchor portion opposite the member portion, the force applicator operatively coupled to the hand engagement member proximate its member portion and operatively coupled to the anchor proximate its anchor portion; and a force application mechanism operatively coupled to the anchor and configured to apply a force to the non-rigid force applicator causing the hand engagement member to manipulate the hand of the user to provide the pronation or supination assistance.

2. The device of claim 1, wherein the hand engagement member is configured to receive and engage only the hand of the user without engaging a wrist or a forearm of the user.

3. The device of claim 1, wherein the hand engagement member is configured to receive and engage the hand of the user and remain engaged with the hand of the user as the force is applied by the force applicator and the force application mechanism.

4. The device of claim 3, wherein the hand engagement member is configured to move from a first engaged position to a second engaged position when the force is applied by the force application mechanism.

5. The device of claim 3, wherein:
the anchor comprises an anchor hand-facing surface;
the hand engagement member, when engaging the hand of the user, engages at least a portion of a palm side or at least a portion of a dorsal side of the hand of the user, and defines an engagement plane substantially parallel with a frontal plane of the hand of the user; and
the anchor hand-facing surface and the engagement plane define an engagement angle.

6. The device of claim 5,
wherein the engagement angle is a first value when the hand engagement member is in the first engaged position;
wherein the engagement angle is a second value when the hand engagement member is in the second engaged position; and
wherein the first value is greater than the second value, thereby providing pronation or supination assistance to the wrist of the user when the hand engagement member is moved from the first engaged position to the second engaged position.

7. The device of claim 6, wherein the hand engagement member, when engaging the hand of the user, engages at least a portion of the palm side, at least a portion of the ulnar side and at least a portion of the dorsal side of the hand of the user, thereby forming a hand receptacle.

8. The device of claim 7, wherein the hand receptacle comprises:
a substantially planar palm portion configured to engage at least a portion of the palm side of the hand of the user;
a U-shaped ulnar portion connected to the palm portion, the ulnar portion configured to engage at least a portion of the ulnar side of the hand of the user; and
a substantially planar dorsal portion connected to the ulnar portion, the dorsal portion configured to engage at least a portion of the dorsal side of the hand of the user.

9. The device of claim 6, wherein:
when the hand engagement member is moved from the first engaged position to the second engaged position, the hand engagement member causes the hand to rotate or move in an arcuate or substantially arcuate range of motion substantially about a longitudinal axis of an arm of the user.

10. The device of claim 9, wherein:
when the hand engagement member is moved from the first engaged position to the second engaged position, the hand engagement member allows the hand to rotate or move in an arcuate or substantially arcuate range of motion about one or more axes other than the longitudinal axis of the arm of the user.

11. The device of claim 9, wherein:
when the hand engagement member is moved from the first engaged position to the second engaged position, the hand engagement member allows the hand to move in a natural range of motion as the arm is pronated or supinated.

12. The device of claim 6, wherein the movement from the first engaged position to the second engaged position comprises rotational or arcuate movement substantially about the longitudinal axis of the arm of the user or substantially about an axis parallel to the longitudinal axis of the arm of the user.

13. The device of claim 1, further comprising:
an attachment member that operatively couples the hand engagement member to the anchor.

14. The device of claim 1, wherein the force application mechanism comprises a rotary mechanism.

15. The device of claim 14, wherein the rotary mechanism, when turned, applies the force in a continuous or non-incremental fashion.

16. The device of claim 14, wherein the rotary mechanism, when turned, applies the force in an incremental fashion.

17. The device of claim 14, wherein the rotary mechanism comprises a non-incremental rotary friction lock mechanism.

18. The device of claim 14, wherein the rotary mechanism comprises a non-incremental rotary harmonic mechanism.

19. A device for manipulating a hand of a user to provide rotational or arcuate pronation or supination assistance about a longitudinal axis or about an axis parallel to the longitudinal axis of an arm of the user, the device comprising:
an anchor;
a hand engagement member configured to receive and engage the hand of the user;
a flexible tethering member connecting the anchor to the hand engagement member
a non-rigid force applicator comprising a member portion and an anchor portion opposite the member portion, the non-rigid force applicator attached to the hand engagement member proximate its member portion and attached to the anchor proximate its anchor portion; and
a force application mechanism attached to the anchor and configured to apply a force to the non-rigid force applicator causing the hand engagement member to manipulate the hand of the user to provide pronation or supination assistance.

20. A method for manipulating a hand of a user to provide pronation or supination assistance, the method comprising:
engaging the hand of the user using a hand engagement member; and
applying a force to the hand engagement member using a non-rigid force applicator to urge the hand engagement member to rotate about a longitudinal axis of an arm of the user, using a force application mechanism to apply force to the non-rigid force applicator operatively coupled with the force application mechanism and the hand engagement member, thereby providing pronation or supination assistance.

* * * * *